(12) United States Patent
Tseng

(10) Patent No.: US 11,707,492 B2
(45) Date of Patent: Jul. 25, 2023

(54) FETAL SUPPORT TISSUE PRODUCTS AND METHODS OF USE

(71) Applicant: BioTissue Holdings, Inc., Miami, FL (US)

(72) Inventor: Scheffer Tseng, Pinecrest, FL (US)

(73) Assignee: BIOTISSUE HOLDINGS INC., Miami, FL (US)

( * ) Notice: Subject to any disclaimer, the term of this patent is extended or adjusted under 35 U.S.C. 154(b) by 168 days.

(21) Appl. No.: 16/063,025

(22) PCT Filed: Jan. 27, 2017

(86) PCT No.: PCT/US2017/015325
§ 371 (c)(1),
(2) Date: Jun. 15, 2018

(87) PCT Pub. No.: WO2017/132503
PCT Pub. Date: Aug. 3, 2017

(65) Prior Publication Data
US 2019/0001021 A1    Jan. 3, 2019

Related U.S. Application Data

(60) Provisional application No. 62/288,881, filed on Jan. 29, 2016.

(51) Int. Cl.
| | |
|---|---|
| *A61K 35/51* | (2015.01) |
| *A61L 27/60* | (2006.01) |
| *A61L 27/36* | (2006.01) |
| *A61K 35/50* | (2015.01) |

(52) U.S. Cl.
CPC ............. *A61K 35/51* (2013.01); *A61K 35/50* (2013.01); *A61L 27/3604* (2013.01); *A61L 27/365* (2013.01); *A61L 27/367* (2013.01); *A61L 27/3645* (2013.01); *A61L 27/3654* (2013.01); *A61L 27/3662* (2013.01); *A61L 27/3666* (2013.01); *A61L 27/3675* (2013.01); *A61L 27/3683* (2013.01); *A61L 27/60* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,069,307 A | 1/1978 | Higuchi et al. |
| 4,077,407 A | 3/1978 | Theeuwes et al. |
| 4,100,022 A | 7/1978 | Ogasa et al. |
| 4,120,649 A | 10/1978 | Schechter |
| 4,201,211 A | 5/1980 | Chandrasekaran et al. |
| 4,230,105 A | 10/1980 | Harwood |
| 4,292,299 A | 9/1981 | Suzuki et al. |
| 4,292,303 A | 9/1981 | Keith et al. |
| 4,305,502 A | 12/1981 | Gregory et al. |
| 4,327,725 A | 5/1982 | Cortese et al. |
| 4,347,841 A | 9/1982 | Benyo et al. |
| 4,405,616 A | 9/1983 | Rajadhyaksha |
| 4,476,116 A | 10/1984 | Anik |
| 4,599,084 A | 7/1986 | Nashef |
| 4,624,848 A | 11/1986 | Lee |
| 4,829,000 A | 5/1989 | Kleinman et al. |
| 4,871,549 A | 10/1989 | Ueda et al. |
| 4,968,509 A | 11/1990 | Radebaugh et al. |

(Continued)

FOREIGN PATENT DOCUMENTS

| | | |
|---|---|---|
| CN | 1903073 A | 1/2007 |
| CN | 103874762 A | 6/2014 |

(Continued)

OTHER PUBLICATIONS

Parsons et al, The American Journal Surgery, 2004, vol. 188, Iss 1, suppl 1, pp. 57-66. (Year: 2004).*
Werber et al, Journal of Foot and Ankle Surgery, 2013, vol. 52, Iss 5, pp. 615-621. (Year: 2013).*
Frykberg et al, Clinics in Podiatric Medicine and Surgery, 2007, 24(3):469-482. (Year: 2007).*
"Particulate." Merriam-Webster.com Dictionary, Merriam-Webster, https://www.merriam-webster.com/dictionary/particulate. Accessed Oct. 23, 2021. (Year: 2021).*
"Minute." Merriam-Webster.com Dictionary, Merriam-Webster, https://www.merriam-webster.com/dictionary/minute. Accessed Oct. 23, 2021. (Year: 2021).*
Bakhach, Organogenesis, 2009, vol. 5, No. 3, pp. 119-126. (Year: 2009).*

(Continued)

*Primary Examiner* — Allison M Fox
(74) *Attorney, Agent, or Firm* — Wilson Sonsini Goodrich & Rosati

(57) ABSTRACT

Methods of treating a complex wound by administering to a complex wound in the individual a therapeutically effective amount of a fetal support tissue product to treat the complex wound. Methods of treating a complex lower extremity ulcer by administering to a complex lower extremity ulcer in the individual a therapeutically effective amount of a fetal support tissue product to treat the complex lower extremity ulcer. Methods of reducing or preventing scar formation from granulation tissue by administering a fetal support tissue product to granulation tissue. Methods of repairing a spina bifida defect by administering to the defect in the individual a therapeutically effective amount of an umbilical cord product.

26 Claims, 3 Drawing Sheets

(56) References Cited

U.S. PATENT DOCUMENTS

| | | |
|---|---|---|
| 4,997,425 A | 3/1991 | Shioya et al. |
| 5,002,071 A | 3/1991 | Harrell |
| 5,011,692 A | 4/1991 | Fujioka et al. |
| 5,017,381 A | 5/1991 | Maruyama et al. |
| 5,033,252 A | 7/1991 | Carter |
| 5,052,558 A | 10/1991 | Carter |
| 5,093,487 A | 3/1992 | Brown et al. |
| 5,116,817 A | 5/1992 | Anik |
| 5,135,915 A | 8/1992 | Czarniecki et al. |
| 5,192,744 A | 3/1993 | Bouck et al. |
| 5,229,135 A | 7/1993 | Philippon et al. |
| 5,260,068 A | 11/1993 | Chen |
| 5,260,069 A | 11/1993 | Chen |
| 5,294,446 A | 3/1994 | Schlameus et al. |
| 5,323,907 A | 6/1994 | Kalvelage |
| 5,336,168 A | 8/1994 | Sibalis |
| 5,352,668 A | 10/1994 | Burgeson et al. |
| 5,436,135 A | 7/1995 | Tayot et al. |
| 5,437,287 A | 8/1995 | Phillips et al. |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,554,593 A | 9/1996 | Nakaya et al. |
| 5,567,441 A | 10/1996 | Chen |
| 5,622,721 A | 4/1997 | Dansereau et al. |
| 5,665,378 A | 9/1997 | Davis et al. |
| 5,686,105 A | 11/1997 | Kelm et al. |
| 5,700,410 A | 12/1997 | Nakamichi et al. |
| 5,837,280 A | 11/1998 | Kenealy et al. |
| 5,837,284 A | 11/1998 | Mehta et al. |
| 5,840,329 A | 11/1998 | Bai |
| 5,869,090 A | 2/1999 | Rosenbaum |
| 5,932,545 A | 8/1999 | Henkin et al. |
| 5,948,766 A | 9/1999 | Milan et al. |
| 5,977,175 A | 11/1999 | Lin |
| 6,046,160 A | 4/2000 | Obi-Tabot |
| 6,152,142 A | 11/2000 | Tseng |
| 6,203,755 B1 | 3/2001 | Odland |
| 6,326,019 B1 | 12/2001 | Tseng |
| 6,328,765 B1 | 12/2001 | Hardwick et al. |
| 6,391,452 B1 | 5/2002 | Antonsen et al. |
| 6,465,014 B1 | 10/2002 | Moroni et al. |
| 6,521,179 B1 | 2/2003 | Girardot et al. |
| 6,573,249 B2 | 6/2003 | Lezdey et al. |
| 6,632,648 B1 | 10/2003 | Kampinga et al. |
| 6,923,983 B2 | 8/2005 | Morgan et al. |
| 6,929,801 B2 | 8/2005 | Klose et al. |
| 6,932,983 B1 | 8/2005 | Straub et al. |
| 6,946,144 B1 | 9/2005 | Jordan |
| 8,071,135 B2 | 12/2011 | Liu et al. |
| 8,105,634 B2 | 1/2012 | Liu et al. |
| 8,153,162 B2 | 4/2012 | Tseng et al. |
| 8,182,840 B2 | 5/2012 | Tseng et al. |
| 8,182,841 B2 | 5/2012 | Tseng et al. |
| 8,187,639 B2 | 5/2012 | Tseng et al. |
| 8,323,701 B2 | 12/2012 | Daniel et al. |
| 8,372,437 B2 | 2/2013 | Daniel |
| 8,420,126 B2 | 4/2013 | Tseng et al. |
| 8,440,235 B2 | 5/2013 | Tseng et al. |
| 8,455,009 B2 | 6/2013 | Tseng et al. |
| 8,460,714 B2 | 6/2013 | Tseng et al. |
| 8,840,665 B2 | 9/2014 | Young et al. |
| 8,932,805 B1 | 1/2015 | Brahm |
| 8,961,617 B2 | 2/2015 | Young |
| 8,980,630 B2 | 3/2015 | Woodbury et al. |
| 9,161,954 B2 | 10/2015 | Tseng et al. |
| 9,161,955 B2 | 10/2015 | Tseng et al. |
| 9,161,956 B2 | 10/2015 | Tseng et al. |
| 9,162,011 B2 | 10/2015 | Stilwell et al. |
| 9,180,145 B2 | 11/2015 | Brown et al. |
| 9,198,939 B2 | 12/2015 | Tseng et al. |
| 9,498,327 B1 | 11/2016 | Brahm |
| 9,526,770 B2 | 12/2016 | Tseng et al. |
| 9,662,355 B2 | 5/2017 | Koob et al. |
| 9,675,733 B2 | 6/2017 | Tseng et al. |
| 9,682,044 B2 | 6/2017 | Tseng et al. |
| 9,694,109 B1 | 7/2017 | Brahm |
| 9,724,370 B2 | 8/2017 | Tseng et al. |
| 9,750,771 B2 | 9/2017 | Tseng et al. |
| 9,750,772 B2 | 9/2017 | Tseng et al. |
| 9,795,639 B1 | 10/2017 | Brahm |
| 9,801,975 B2 | 10/2017 | Stilwell et al. |
| 9,801,976 B2 | 10/2017 | Stilwell et al. |
| 9,803,176 B2 | 10/2017 | Patel et al. |
| 9,814,746 B2 | 11/2017 | Werber et al. |
| 9,821,013 B2 | 11/2017 | McFetridge et al. |
| 9,827,293 B2 | 11/2017 | Koob et al. |
| 9,913,466 B2 | 3/2018 | Chang et al. |
| 9,919,078 B1 | 3/2018 | Brahm |
| 9,920,301 B2 | 3/2018 | Taghizadeh |
| 9,944,900 B2 | 4/2018 | Gage et al. |
| 9,956,248 B2 | 5/2018 | Tom et al. |
| 9,956,252 B2 | 5/2018 | Tseng et al. |
| 9,993,506 B2 | 6/2018 | Brahm |
| 10,006,003 B2 | 6/2018 | Spencer et al. |
| 10,029,030 B2 | 7/2018 | Koob et al. |
| 10,039,793 B2 | 8/2018 | Brown et al. |
| 10,105,397 B2 | 10/2018 | Morse et al. |
| 10,105,398 B2 | 10/2018 | Morse et al. |
| 10,220,059 B2 | 3/2019 | Kihm et al. |
| 10,314,688 B2 | 6/2019 | Shepard et al. |
| 10,413,635 B2 | 9/2019 | Namin et al. |
| 10,568,914 B1 | 2/2020 | Brahm |
| 10,576,104 B2 | 3/2020 | Tom et al. |
| 10,583,219 B1 | 3/2020 | Brahm |
| 10,610,545 B2 | 4/2020 | Aberman |
| 10,646,519 B2 | 5/2020 | Tom et al. |
| 10,688,220 B2 | 6/2020 | Hopkinson et al. |
| 2001/0041684 A1 | 11/2001 | Lezdey et al. |
| 2003/0064093 A1 | 4/2003 | Jordan |
| 2003/0180181 A1 | 9/2003 | Greib et al. |
| 2003/0187515 A1 | 10/2003 | Hariri et al. |
| 2004/0043026 A1 | 3/2004 | Tuan et al. |
| 2004/0057938 A1 | 3/2004 | Ghinelli |
| 2004/0059430 A1 | 3/2004 | Kim et al. |
| 2004/0126323 A1 | 7/2004 | Shevchuk et al. |
| 2004/0180822 A1 | 9/2004 | Grafton |
| 2004/0181240 A1 | 9/2004 | Tseng et al. |
| 2005/0064391 A1 | 3/2005 | Segal et al. |
| 2006/0078993 A1 | 4/2006 | Phan et al. |
| 2006/0193769 A1 | 8/2006 | Nelson et al. |
| 2007/0048292 A1 | 3/2007 | Morita et al. |
| 2007/0071740 A1 | 3/2007 | Tseng et al. |
| 2007/0202189 A1 | 8/2007 | Ahlfors et al. |
| 2007/0231401 A1 | 10/2007 | Tseng et al. |
| 2008/0046095 A1 | 2/2008 | Daniel |
| 2008/0050814 A1 | 2/2008 | Allickson |
| 2008/0069895 A1 | 3/2008 | Liu et al. |
| 2008/0102135 A1 | 5/2008 | Ollivier |
| 2008/0131522 A1 | 6/2008 | Liu et al. |
| 2008/0181935 A1 | 7/2008 | Bhatia et al. |
| 2008/0181967 A1 | 7/2008 | Liu et al. |
| 2008/0193554 A1 | 8/2008 | Dua et al. |
| 2008/0241211 A1 | 10/2008 | Han et al. |
| 2009/0130162 A2 | 5/2009 | Pathak et al. |
| 2010/0047214 A1 | 2/2010 | Abramson et al. |
| 2010/0104539 A1 | 4/2010 | Daniel et al. |
| 2010/0272782 A1 | 10/2010 | Owens et al. |
| 2010/0298229 A1 | 11/2010 | Boyle et al. |
| 2011/0212158 A1 | 9/2011 | Tom et al. |
| 2011/0256202 A1 | 10/2011 | Tom et al. |
| 2011/0307059 A1 | 12/2011 | Young et al. |
| 2011/0311491 A1 | 12/2011 | Edinger et al. |
| 2012/0010708 A1 | 1/2012 | Young et al. |
| 2012/0010727 A1 | 1/2012 | Young et al. |
| 2012/0020933 A1 | 1/2012 | Young et al. |
| 2012/0035743 A1 | 2/2012 | Young et al. |
| 2012/0035744 A1 | 2/2012 | Young et al. |
| 2012/0141595 A1 | 6/2012 | Tseng et al. |
| 2012/0207848 A1 | 8/2012 | Tseng et al. |
| 2012/0207849 A1 | 8/2012 | Tseng et al. |
| 2012/0263731 A1 | 10/2012 | Fraunhofer et al. |
| 2012/0269880 A1 | 10/2012 | Tseng et al. |

(56) References Cited

U.S. PATENT DOCUMENTS

| | | |
|---|---|---|
| 2012/0294909 A1 | 11/2012 | Daniel et al. |
| 2012/0294910 A1 | 11/2012 | Daniel et al. |
| 2012/0328690 A1 | 12/2012 | Tseng et al. |
| 2013/0156863 A1 | 6/2013 | Tseng et al. |
| 2013/0197665 A1 | 8/2013 | Daniel et al. |
| 2013/0209524 A1 | 8/2013 | Young |
| 2013/0211502 A1 | 8/2013 | Young |
| 2013/0211504 A1 | 8/2013 | Young |
| 2013/0211511 A1 | 8/2013 | Young |
| 2013/0218274 A1* | 8/2013 | Spencer ............. A61F 2/105 623/15.12 |
| 2013/0236506 A1 | 9/2013 | Young |
| 2013/0238100 A1 | 9/2013 | Young |
| 2013/0289724 A1 | 10/2013 | Young |
| 2013/0344162 A1 | 12/2013 | Morse et al. |
| 2013/0344163 A1 | 12/2013 | Tseng et al. |
| 2014/0050788 A1 | 2/2014 | Daniel et al. |
| 2014/0052247 A1 | 2/2014 | Daniel et al. |
| 2014/0052274 A1 | 2/2014 | Koob et al. |
| 2014/0106447 A1 | 4/2014 | Brown et al. |
| 2014/0112998 A1* | 4/2014 | Tseng ............. A61L 27/54 424/583 |
| 2014/0205646 A1 | 7/2014 | Morse et al. |
| 2014/0255496 A1 | 9/2014 | Daniel et al. |
| 2014/0255508 A1 | 9/2014 | Morse et al. |
| 2014/0271776 A1 | 9/2014 | Vines et al. |
| 2014/0294777 A1* | 10/2014 | Tom ............. A61K 38/57 424/93.7 |
| 2014/0294780 A1 | 10/2014 | McFetridge et al. |
| 2014/0302162 A1 | 10/2014 | Morse et al. |
| 2014/0348940 A1 | 11/2014 | Murphy et al. |
| 2015/0017255 A1 | 1/2015 | Koob et al. |
| 2015/0086634 A1 | 3/2015 | Koob et al. |
| 2015/0216912 A1 | 8/2015 | Koob |
| 2015/0250829 A1 | 9/2015 | Daniel et al. |
| 2015/0320906 A1 | 11/2015 | Broussard et al. |
| 2015/0328264 A1 | 11/2015 | Lucey et al. |
| 2015/0335686 A1 | 11/2015 | Spencer et al. |
| 2015/0335771 A1 | 11/2015 | Tseng et al. |
| 2016/0066566 A1 | 3/2016 | Chang et al. |
| 2016/0067287 A1 | 3/2016 | McQueen et al. |
| 2016/0082152 A1 | 3/2016 | Brahm |
| 2016/0106785 A1 | 4/2016 | Tseng et al. |
| 2016/0184368 A1 | 6/2016 | Tseng et al. |
| 2016/0193253 A1 | 7/2016 | Petrucci |
| 2016/0303171 A1 | 10/2016 | Tseng et al. |
| 2016/0324902 A1 | 11/2016 | Tseng et al. |
| 2016/0346332 A1 | 12/2016 | Spencer et al. |
| 2017/0027993 A1 | 2/2017 | Ichim |
| 2017/0095515 A1 | 4/2017 | Beaudry et al. |
| 2017/0136071 A1 | 5/2017 | Danilkovitch et al. |
| 2017/0203004 A1 | 7/2017 | Murphy et al. |
| 2017/0239389 A1 | 8/2017 | Tseng et al. |
| 2017/0252380 A1 | 9/2017 | Cox, Jr. et al. |
| 2017/0260500 A1 | 9/2017 | Goodman et al. |
| 2017/0326182 A1 | 11/2017 | Tseng et al. |
| 2017/0368105 A1 | 12/2017 | Sinclair et al. |
| 2018/0008649 A1 | 1/2018 | Aberman et al. |
| 2018/0017577 A1 | 1/2018 | Franco |
| 2018/0055622 A1 | 3/2018 | Tokish et al. |
| 2018/0059109 A1 | 3/2018 | Hsuan et al. |
| 2018/0110900 A1 | 4/2018 | Korenfeld |
| 2018/0112184 A1 | 4/2018 | Kim et al. |
| 2018/0117121 A1 | 5/2018 | Koob et al. |
| 2018/0119093 A1 | 5/2018 | Kukharchuk et al. |
| 2018/0126036 A1 | 5/2018 | Early |
| 2018/0127721 A1 | 5/2018 | Phan |
| 2018/0132908 A1 | 5/2018 | Brahm et al. |
| 2018/0133261 A1 | 5/2018 | Herzberg et al. |
| 2018/0140641 A1 | 5/2018 | Harrell |
| 2018/0163177 A1 | 6/2018 | Lo et al. |
| 2018/0177716 A1 | 6/2018 | Noh et al. |
| 2018/0177989 A1 | 6/2018 | Prentice |
| 2018/0193387 A1 | 7/2018 | Tseng et al. |
| 2018/0221418 A1 | 8/2018 | Daniel et al. |
| 2018/0264049 A1 | 9/2018 | Wagner et al. |
| 2018/0271914 A1 | 9/2018 | Steed et al. |
| 2018/0271917 A1 | 9/2018 | Fu |
| 2018/0338998 A1 | 11/2018 | Petrucci |
| 2018/0344777 A1 | 12/2018 | Harris et al. |
| 2018/0344900 A9 | 12/2018 | Brown et al. |
| 2018/0346874 A1 | 12/2018 | Harris et al. |
| 2018/0362920 A1 | 12/2018 | Guo |
| 2018/0362923 A1 | 12/2018 | Guo |
| 2018/0362932 A1 | 12/2018 | Guo |
| 2019/0040355 A1 | 2/2019 | Woodbury et al. |
| 2019/0046585 A1 | 2/2019 | Morse et al. |
| 2019/0070335 A1 | 3/2019 | Karagianis |
| 2019/0127702 A1 | 5/2019 | Kerkis et al. |
| 2019/0134100 A1 | 5/2019 | Cao et al. |
| 2019/0134265 A1 | 5/2019 | Semler et al. |
| 2019/0141987 A1 | 5/2019 | Patel et al. |
| 2019/0177684 A1 | 6/2019 | Ha et al. |
| 2020/0069739 A1 | 3/2020 | Tom et al. |
| 2020/0077987 A1 | 3/2020 | Harrell |
| 2020/0129563 A1 | 4/2020 | Flower |
| 2020/0147144 A1 | 5/2020 | White et al. |
| 2020/0179566 A1 | 6/2020 | Liu et al. |

FOREIGN PATENT DOCUMENTS

| | | |
|---|---|---|
| EP | 0669138 A2 | 8/1995 |
| EP | 1604695 A1 | 12/2005 |
| JP | 74043153 B | 11/1974 |
| JP | H01256967 A | 10/1989 |
| KR | 20010098716 A | 11/2001 |
| WO | WO-9837903 A1 | 9/1998 |
| WO | WO-03077794 A2 | 9/2003 |
| WO | WO-03097809 A2 | 11/2003 |
| WO | WO-2004026244 A2 | 4/2004 |
| WO | WO-2004060388 A1 | 7/2004 |
| WO | WO-2005060988 A1 | 7/2005 |
| WO | WO-2006094247 A2 | 9/2006 |
| WO | WO-2007071048 A1 | 6/2007 |
| WO | WO-2011031489 A2 | 3/2011 |
| WO | WO-2017132503 A1 | 8/2017 |

OTHER PUBLICATIONS

Willem F. Wolkers and Harrie tte Oldenhof (eds.), Cryopreservation and Freeze-Drying Protocols, Methods in Molecular Biology, vol. 2180, https://doi.org/10.1007/978-1-0716-0783-1_1, © Springer Science+Business Media, LLC, part of Springer Nature 2021 (Year: 2021).*

Lavery et al, International Wound Journal, 2014, vol. 11, Issue 5, pp. 554-560, (Year: 2014).*

Frykberg et al, International Wound Journal, 2017, vol. 14, Issue 3, pp. 569-577. (Year: 2017).*

Simman et al, Journal of the American College of Clinical Wound Specialists, 2017, vol. 9, pp. 1-9. (Year: 2017).*

Shores et al, Journal of Plastic, Reconstructive & Aesthetic Surgery, 2012, vol. 65, pp. 1544-1550. (Year: 2012).*

Ahmed et al. Expression and localization of alphavbeta6 integrin in extraplacental fetal membranes: possible role in human parturition. Mol Hum Reprod 10(3):173-179 (2004).

Allred et al. A novel ELISA for measuring CD36 protein in human adipose tissue. J Lipid Res 2(2):408-415 (2011).

Azuara-Blanco et al. Amniotic Membrane Transplantation for Ocular Surface Reconstruction. Br. J. Ophthalmol. 83(4):399-402 (1999).

Azuara-Blanco et al. Amniotic Membrane Transplantation for Ocular Surface Reconstruction. Invest. Ophthalmol. Vis. Sci. 39(4):S428 (1998).

Bae et al. Characterization of the Promoter Region of the Human Transforming Growth Factor-β Type II Receptor Gene. J. Biol. Chem. 270(49):29460-29468 (1995).

Barton et al. Amniotic membrane transplantation in glaucoma surgery. Invest Ophthalmol Vis Sci 38:S473 (1997).

Becker. Patch Work—New Hope for spina bifida's youngest patients. TMC Pulse 3(9):25-27 (Oct. 2016).

(56) References Cited

OTHER PUBLICATIONS

Bhutto et al. Localization of Collagen XVIII and the Endostatin Portion of Collagen XVIII in Ages Human Control Eyes and Eyes with Age-Related Macular Degeneration. Invest. Ophthalmol. Vis. Sci. 45(5):1544-1552 (2004).
Border et al. Transforming Growth Factor-β in Disease: The Dark Side of Tissue Repair. J. Clin. Invest. 90:1-7 (1992).
Brown et al. In utero repair of myelomeningocele with autologous amniotic membrane in the fetal lamb model. J Pediatr Surg 49(1):133-137 (2014).
Budenz et al. Amniotic Membrane Transplantation for Repair of Leaking Glaucoma Filtering Blebs. Am. J. Ophthalmol. 130:580-588 (2000).
Chen et al. Functions of hyaluronan in wound repair. Wound Rep Reg 7:79-89 (1999).
Chen et al. Recombinant Adenovirus Coexpressing Covalent Peptide/MHC Class II Complex and B7-1: In Vitro and In Vivo Activation of Myelin Basic Protein-Specific T Cells. J. Immunol. 167:1297-1305 (2001).
Cho et al. Conjunctival Epithelial Cells Cultured on Human Amniotic Membrane Do Not Transdifferentiate into Corneal Epithelial Type Cells. Invest. Ophthalmol. Vis. Sci. 39(4):S428 (1998).
Cho et al. Conjunctival Epithelial Cells Cultured on Human Amniotic Membrane Fail To Transdifferentiate into Corneal Epithelial-type Cells. Cornea 18:216-224 (1999).
Choi et al. Effect of the Application of Human Amniotic Membrane on Rabbit Corneal wound Healing After Excimer Laser Photorefractive Keratectomy. Cornea 17:389-395 (1998).
Colon et al. Transfer of Inter-α-inhibitor Heavy Chains to Hyaluronan by Surface-linked Hyaluronan-TSG-6 Complexes. J. Biol. Chem. 2009. 284:2320-2331.
Cooke et al. Comparison of cryopreserved amniotic membrane and umbilical cord tissue with dehydrated amniotic membrane/chorion tissue. J Wound Care 23(10):465-474 (2014).
Day et al. Hyaluronan cross-linking: a protective mechanism in inflammation? Trends in Immunology 26(12):637-643 (2005).
Derotth. Plastic Repair of Conjunctival Defects with Fetal Membranes. Archives of Ophthalmology 23:522-525 (1940).
Derynk et al. TGF-β receptor signaling. Biochem. Biophys. Acta. 1333:F105-F150 (1997).
Diaz-Prado et al. Potential use of the human amniotic membrane as a scaffold in human articular cartilage repair. Cell Tissue Bank 11:183-195 (2010).
Dua et al. Amniotic Membrane Transplantation. Br. J. Ophthalmol. 83:748-752 (1999).
English Translation of JP74043153B (App. S45-107284) (9 pgs.) (Pub. Nov. 19, 1974).
Ericsson et al. Chapter 17: Protein extraction from solid tissue. Methods Mol Biol. 675:307-312 (2011).
Fiorito et al. Chapter 14: Surgical Management of Diabetic Foot Ulcers. Surgical Wound Healing and Management (pp. 128-142) (2012).
Fortunato et al. Interleukin-10 and transforming growth factor-β inhibit amniochorion tumor necrosis factor-α production by contrasting mechanisms of action: Therapeutic implications in prematurity. Am. J. Obstet. Gynecol. 177(4):803-809 (1997).
Fortunato et al. Interleukin-10 inhibition of interleukin-6 in human amniochorionic membrane: Transcriptional regulation. Am. J. Obstet. Gynecol. 175:1057-1065 (1996).
Fortunato et al. The effect of transforming growth factor and interleukin-10 on interleukin-8 release by human amniochorion may regulate histologic chorioamnionitis. Am. J. Obstet. Gynecol. 179(3):794-799 (1998).
Franch et al. Human Amniotic Membrane Transplantation. Invest. Ophthalmol. Vis. Sci. 39(4):S90 (1998).
Fries et al. Inter-alpha-inhibitor, hyaluronan and inflammation. Acta Biochim Polonica 50(3):735-742 (2003).
Fujishima et al. Trabeculectomy With the Use of Amniotic Membrane for Uncontrolled Glaucoma, Ophthalmic. Surg. Lasers 29:428-431 (1998).

Fukuda et al. Differential Distribution of Subchains of the Basement Membrane Components Type IV Collagen and Laminin Among the Amniotic Membrane, Cornea, and Conjunctiva. Cornea 18:73-79 (1999).
Gabbiani. The myofibroblast in wound healing and fibrocontractive diseases. J. Pathol. 200:500-503 (2003).
Grande. Role of Transforming Growth Factor-β in Tissue Injury and Repair. Proc. Soc. Exp. Biol. Med. 214:27-40 (1997).
Guo. Carbopol® Polymers for Pharmaceutical Drug Delivery Applications. Drug Delivery Technology 3(6):1-4 (2003).
Hales et al. TGF-β-1 induces lens cells to accumulate α-smooth muscle actin, a marker for subcapsular cataracts. Curr. Eye Res. 13:885-890 (1994).
Hall et al. Liquid Extraction Surface Analysis Mass Spectrometry Method for Identifying the Presence and Severity of Nonalcoholic Fatty Liver Disease. Anal. Chem. 89(9):5161-5170 (2017).
Hanada et al. Regulation of cytokine signaling and inflammation. Cytokine & Growth Factor Reviews 13(4-5):413-421 (2002).
Hao et al. Identification of Antiangiogenic and Antiinflammatory Proteins in Human Amniotic Membrane. Cornea 19(3):348-352 (2000).
Hatano et al. Transplantation of amniotic membrane and limbal autograft in the treatment of recurrent pterygium. Clinical Ophthalmology 50(6):1101-1104 (1996) (English Abstract).
He et al. A simplified system for generating recombinant adenoviruses. PNAS USA 95:2509-2514 (1998).
He et al. Biochemical Characterization and Function of Complexes formed by Hyaluronan and the Heavy Chains of Inter-α-inhibitor (HC-HA) Purified from Extracts of Human Amniotic Membrane. J Biol Chem 284(30):20136-20146 (Jul. 24, 2009).
He et al. Immobilized heavy chain-hyaluronic acid polarizes lipopolysaccharide-activated macrophages toward M2 phenotype. J Biol Chem 288(36):25792-25803 (2013).
He et al. Inhibition of Proliferation and Epithelial Mesenchymal Transition via Wnt and TGF-β Signaling Pathway in an in vitro Cell Culture Based-PVR Model by HC-HA/PTX3 Purified from Amniotic Membrane. The Association for Research in Vision and Ophthalmology (ARVO) 2016 on May 1-May 5 (Washington State Convention Center, Seattle, Washington) Abstract No. 5384-B005 (2 pgs).
He et al. Suppression of activation and induction of apoptosis in RAW264.7 cells by amniotic membrane extract. Invest Ophthalmol. Vis. Sci. 49:4468-4475 (2008).
Hilmy et al. Physical and chemical properties of freeze-dried amnio-chorion membranes sterilized by γ irradiation. Atom Indonesia 13(2):1-3 (1987) Abstract only.
Hori. Amniotic Membrane Transplantation and Immune Reaction. Folia Ophthalmologica Japonica 56(9):722-727 (2005) (English Abstract).
Howes et al. Receptor for Advanced Glycation End Products and Age-Related Macular Degeneration. Invest. Ophthalmol. Vis. Sci. 45(10):3713-3720 (2004).
Huang et al. A Serum-derived Hyaluronan-associated Protein (SHAP) Is the Heavy Chain of the Inter a-Trypsin Inhibitor. J Biol Chem 268(35):26725-76730 (1993).
Jester et al. Corneal Stromal Wound Healing in Refractive Surgery: the Role of Myofibroblasts. Prog. Retin. Eye Res. 18(3):311-356 (1999).
Jester et al. Induction of α-Smooth Muscle Actin Expression and Myofibroblast Transformation in Cultured Cornea Keratocytes. Cornea 15(5):505-516 (1996).
Keelan et al. Activin A Exerts both Pro- and -Anti-inflammatory Effects on Human Term Gestational Tissues. Placenta 21:38-43 (2000).
Kida et al. The SHAP-HA complex in sera from patients with rheumatoid arthritis and osteoarthritis. J Rheumatol 26(6):1230-1238 (1999).
Kim et al. Amniotic Membrane Patching Promotes Healing and Inhibits Protease Activity on Wound Healing Following Acute Corneal Alkali Burns. Exp. Eye Res. 70:329-337 (1998).
Kim et al. Clinical Uses of Human Amniotic Membrane for Ocular Surface Diseases. In: Advances in Corneal Research, Lass, J.H. ed. (NY: Plenum Press), pp. 117-134 (1997).

(56) References Cited

OTHER PUBLICATIONS

Kim et al. Temporary Amniotic Membrane Graft Promotes Healing and Inhibits Protease Activity in Corneal Wound Induced by Alkali Burn in Rabbits. Invest. Ophthalmol. Vis. Sci. 39(4):S90 (1998).
Kim et al. The Effects on Inhibition of Corneal Neovascularization After Human Amniotic Membrane Transplantation in Severely Damaged Rabbit Corneas. Korean J. Ophthalmol. 9:32-46 (1995).
Kim et al. Transplantation of preserved human amniotic membrane for surface reconstruction in severely damaged rabbit corneas. Cornea 14:473-484 (1995).
Kishida et al. Hyaluronan (HA) and serum-derived hyaluronan-associated protein (SHAP)-HA complex as predictive markers of cervical ripening in premature labor. 49(2):105-108 (2008).
Klen. Influence of Ionizing Sterilization on the Permeability of Human Chorio-Amniotic, Dermo-Epidermal and Fascial Grafts. Res. Exp. Med. 167(1):15-21 (1976).
Koizumi et al. Amniotic Membrane as a Substrate for Cultivating Limbal Corneal Epithelial Cells for Autologous Transplantation in Rabbits. Cornea 19:65-71 (2000).
Koizumi et al. Cultivation of Corneal Epithelial Cells on Intact and Denuded Human Amniotic Membrane. Invest. Ophthalmol. Vis. Sci. 41:2506-2513 (2000).
Koizumi et al. Growth Factor mRNA and Protein in Preserved Human Amniotic Membrane. Curr. Eye Res. 20:173-177 (2000).
Kopp et al. Abrogation of Transforming Growth Factor-beta Signaling by SMAD7 Inhibits Collagen Gel Contraction of Human Dermal Fibroblasts. J. Biol. Chem. 280(22):21570-21576 (2005).
Kruse et al. Cryopreserved Human Amniotic Membrane For Ocular Surface Reconstruction. Graefe's Arch. Clin. Exp. Ophthalmol. 238:68-75 (2000).
Kruse et al. Multilayer Amniotic Membrane Transplantation for Reconstruction of Deep Corneal Ulcers. Ophthalmology 106:1504-1511 (1999).
Kuriyan et al. A potential novel therapy for PVR: HC-HA/PTX3, an active matrix component of amniotic membrane, inhibits proliferation of rabbit RPE cells and is non-toxic intravitreally. The Association for Research in Vision and Ophthalmology (ARVO) 2015 meeting on May 3-May 7(Colorado Convention Center Denver, CO) Abstract No. 1126-B029 (2 pgs).
Kuriyan et al. HC-HA/PTX3, an active matrix component of amniotic membrane, inhibits proliferation and epithelial mesenchymal transition of RPE cells: a potential novel therapy for PVR. The Association for Research in Vision and Ophthalmology (ARVO) 2015 meeting on May 3- May 7 (Colorado Convention Center Denver, CO) Abstract No. 2287-B0192 (2 pgs).
Kuznetsova et al. The N-terminal module of thrombospondin-1 interacts with the link domain of TSG-6 and enhances its covalent association with the heavy chains of inter-alpha-trypsin inhibitor. J Biol Chem 280:30899-30908 (2005).
Lawrence. Transforming Growth Factor-$\beta$: a general review. Eur. Cytokine Netw. 7:363-374 (1996).
Lee et al. Amniotic Membrane Transplantation for Persistent Epithelial Defects with Ulceration. Am. J. Ophthalmol. 123:303-312 (1997).
Lee et al. An Agarose Gel Electrophoretic Method for Analysis of Hyaluronan Molecular Weight Distribution. Anal. Biochem. 219:278-287 (1994).
Lee et al. Suppression of TGF-$\beta$ signaling in both normal conjunctival fibroblasts and pterygial body fibroblasts by amniotic membrane. Curr. Eye Res. 20(4):325-334 (2000).
Li et al. An Experimental Study of the Effects of Human Amniotic Membrane on Human Retinal Pigment Epithelial Cell Proliferation in vitro. Acta Acadamiae Medicinae Militaris Tertia 25(5):407-409 (2003) (English Abstract).
Li et al. Reversal of myofibroblasts by amniotic membrane stromal extract. J Cell Physiol. 215(3):657-664 (2008).
Lieberman et al. Pharmaceutical Dosage Forms. 2 Ed. 1:209-214 (1990).
Liu et al. Biocompatibility and stability of disulfide-crosslinked hyaluronan films. Biomaterials 26(23):4737-4746 (2005).
Liu et al. E-cadherin engagement stimulates proliferation via Rac1. Journal of Cell Biology 173(3):431-441 (2006).
Logan et al. Decorin Attenuates Gliotic Scar Formation in the Rat Cerebral Hemisphere. Exp. Neurol. 159:504-510 (1999).
Ma et al. Amniotic Membrane Graft for Primary Pterygium: Comparison with Conjunctival Autograft and Topical Mitomycin C Treatment. Br. J. Ophthalmol. 84:973-978 (2000).
Marek et al. TGF-$\beta$- (transforming growth factor-$\beta$) in chronic inflammatory conditions—a new diagnostic and prognostic marker? Med. Sci. Monitl. 8(7):RA145-RA151 (2002).
Massague et al. Controlling TGF-$\beta$ signaling. Genes and Development 14:627-644 (2000).
Meller et al. Amniotic Membrane Transplantation for Acute Chemical or Thermal Burns. Ophthalmology. 107:980-990 (2000).
Meller et al. Amniotic Membrane Transplantation for Symptomatic Conjunctivochalasis Refractory to Medical Treatments. Cornea 19:796-803 (2000).
Meller et al. Amniotic Membrane Transplantation in the Human Eye. Deutsches Aerzteblatt Online 108(14):243-248 (2011).
Meller et al. Conjunctival Epithelial Cell Differentiation on Amniotic Membrane. Invest. Ophthalmol. Vis. Sci. 40:878-886 (1999).
Meller et al. In Vitro Conjunctival Epithelial Differentiation on Preserved Human Amniotic Membrane. Invest. Ophthalmol. Vis. Sci. 39(4):S428 (1998).
Merck Manuals Online Medical Library, Age-Related Macular Degeneration (ARMD), originally printed Aug. 13, 2008/reprinted 2016 from http://www.merck.com/mmpe/print/sec09/ch106/ch106b.html (9 pgs.).
Milner et al. TSG-6: a multifunctional protein associated with inflammation. J. Cell Sci. 116(10):1863-1873 (2003).
Moller-Pedersen et al. Neutralizing antibody to TGF-$\beta$ modulates stromal fibrosis but not regression of photoablative effect following PRK. Curr. Eye Res. 17:736-747 (1998).
Mondello et al. In vivo activity of terpenin-4-ol, the main bioactive component of Melaleuca alternifolia Cheel (tea tree) oil against azole-susceptible and -resistant human pathogenic Candida species. BMC Infectious Diseases 6:158 (2006).
Monteleone et al. SMAD7 in TGF-$\beta$-mediated negative regulation of gut inflammation. Trends in Immunology 25(10):513-517 (2004).
Mukhopadhyay et al. Two distinct populations of tumor necrosis factor-stimulated gene-6 protein in the extracellular matrix of expanded mouse cumulus cell-oocyte complexes. Archives of Biochemistry and Biophysics 394(2):173-181 (2001).
Na et al. Analysis of Human Amniotic Membrane Components as Proteinase Inhibitors for Development of Therapeutic Agent for Recalcitrant Keratitis. Trophoblast Res. 13:453-466 (1999).
Na et al. Analysis of Human Amniotic Membrane Components as Proteinase Inhibitors for Development of Therapeutic Agent of Recalcitrant Keratitis. Invest. Ophthalmol. Vis. Sci. 39(4):S90 (1998).
Nakao et al. SMAD7: a new key player in TGF-b-associated disease. Trends in Molecular Medicine 8(8):361-363 (2002).
Neumann et al. High molecular weight hyaluronic acid inhibits advanced glycation endproduct-induced NF-kB activation and cytokine expression. FEBS Ltrs. 453:283-287(1999).
Obayashi et al. Role of serum-derived hyaluronan-associated protein-hyaluronan complex in ovarian cancer. Oncol Rep 19(5):1245-1251 (2008).
Ochsner et al. Decreased expression of tumor necrosis factor-alpha-stimulated gene 6 in cumulus cells of the cyclooxygenase2 and EP2 null mice. Endocrinology 144:1008-1019 (2003).
Oikawa et al. Inhibition of Angiogenesis by 15-Deoxyspergualin. J. Antibiotics 44(9):1033-1035 (1991).
Papanna et al. Cryopreserved Human Umbilical Cord for In Utero Myeloschisis Repair. Neuroreport 128(2):325-330 (2016).
Papanna et al. Cryopreserved human umbilical cord (HUC) as a regenerative patch material for in-utero repair of myelomeningocele (MMC) to preserve neuronal anatomy. American Journal of Obstetrics & Gynecology 212(1):S46-S47 (2015).
Papanna et al. Cryopreserved human umbilical cord patch for in-utero spina bifida repair. Ultrasound Obstet Gynecol 47:168-176 (2016).

(56) References Cited

OTHER PUBLICATIONS

Park et al. Modulation of Acute Inflammation and Keratocyte Death by Suturing, Blood and Amniotic Membrane in PRK. Invest. Ophthalmol. Vis. Sci. 41:2906-2914 (2000).
Park et al. Temperature Cooling Reduces Keratocyte Death in Excimer Laser Ablated Corneal and Skin Wounds. Invest. Ophthalmol. Vis. Sci. 39(4):S449 (1998).
PCT/US2003/07853 International Search Report dated Feb. 26, 2004.
PCT/US2006/37906 International Preliminary Report on Patentability dated Apr. 1, 2008.
PCT/US2006/37906 International Search Report and Written Opinion dated Jul. 11, 2007.
PCT/US2010/46675 International Preliminary Report on Patentability dated Feb. 28, 2012.
PCT/US2010/46675 International Search Report and Written Opinion dated May 30, 2011.
PCT/US2011/042679 International Preliminary Report on Patentability dated Jan. 8, 2013.
PCT/US2011/042679 International Search Report and Written Opinion dated Mar. 9, 2012.
PCT/US2012/035678 International Preliminary Report on Patentability dated Oct. 29, 2013.
PCT/US2012/035678 International Search Report and Written Opinion dated Oct. 1, 2012.
PCT/US2012/052358 International Preliminary Report on Patentability dated Mar. 4, 2014.
PCT/US2012/052358 International Search Report and Written Opinion dated Jan. 31, 2013.
PCT/US2017/015325 International Preliminary Report on Patentability dated Aug. 9, 2018.
PCT/US2017/015325 International Search Report and Written Opinion dated Jun. 9, 2017.
PCT/US2017/015325 Invitation to Pay Additional Fees dated Apr. 10, 2017.
Petraglia et al. Inhibin and Activin in Human Fetal Membranes: Evidence of a Local Effect on Prostaglandin Release. J. Clin. Endocrinol. Metab. 77(2):542-548 (1993).
Pires et al. Amniotic Membrane Transplantation for Symptomatic Bullous Keratopathy. Arch. Ophthalmol. 117(10):1291-1297 (1999).
Pires et al. Amniotic Membrane Transplantation or Limbal Conjunctival Autograft for Limbal Stem Cell Deficiency Induced by 5-fluorouracil in Glaucoma Surgeries. Cornea 19:284-287 (2000).
Prabhasawat et al. Comparison of Conjunctival Autografts, Amniotic Membrane Grafts, and Primary Closure for Pterygium Excision. Ophthalmology 104:974-985 (1997).
Prabhasawat et al. Impression Cytology Study of Epithelial Phenotype of Ocular Surfaces Reconstructed by Preserved Human Amniotic Membrane. Arch Ophthalmol. 115:1360-1367 (Nov. 1997).
Relucenti et al. Cumulus oophorus extracellular matrix in the human oocyte: a role for adhesive proteins. Ital J Anat Embryol 110(2 Supp 1):219-224 (2005).
Riley et al. Production of inhibin forms by the fetal membranes, decidua, placenta and fetus at parturition. Hum. Reprod. 15:578-583 (2000).
Rodriguez-Ares et al. Repair of Scleral Perforation with Preserved Scleral and Amniotic Membrane in Marfan's Syndrome. Ophthalmic Surg. Lasers 30(6):485-487 (1999).
Romero et al. The natural interleukin-1 receptor antagonist in the fetal, maternal, and amniotic fluid compartments: The effect of gestational age, fetal gender, and intrauterine infection. Am. J. Obstet. Gynecol. 171:912-921 (1994).
Ronnov-Jessen et al. Induction of α-Smooth Muscle Actin by Transforming Growth Factor-β1 in Quiescent Human Breast Gland Fibroblasts. Lab. Invest. 68:696-707 (1993).
Rovere et al. The long pentraxin PTX3 binds to apoptotic cells and regulates their clearance by antigen-presenting dendritic cells. Blood 96(13):4300-4306 (2000).
Saltzman. Drug Administration and Drug Effectiveness. Chapter 2. Drug Delivery—Engineering Principles for Drug Therapy. Oxford Press, p. 9-19 (2001).
Salustri et al. PTX3 plays a key role in the organization of the cumulus oophorus extracellular matrix and in in vivo fertilization. Development 131:1577-1586 (2004).
Sato et al. Role of Growth Factors for Ocular Surface Reconstruction After Amniotic Membrane Transplantation. Invest. Ophthalmol. Vis. Sci. 39(4):S428 (1998).
Serini et al. The Fibronectin Domain ED-A Is Crucial for Myofibroblastic Phenotype Induction by Transforming Growth Factor-β1. J. Cell. Biol. 142:873-881 (1998).
Shah et al. Control of scarring in adult wounds by neutralising antibody to transforming growth factor β. Lancet 339:213-214 (1992).
Shen et al. The SHAP-hyaluronan complex in serum from patients with chronic liver diseases caused by hepatitis virus infection. Hepatol Res 34(3):178-186 (2006).
Shimazaki et al. Amniotic Membrane Transplantation for Ocular Surface Reconstruction in Patients with Chemical and Thermal Burns. Ophthalmology. 104(12):2068-2076 (1997).
Shimazaki et al. Transplantation of Amniotic Membrane and Limbal Autograft for Patients with Recurrent Pterygium Associated with Symblepharon. Br. J. Ophthalmol. 82(3):235-240 (1998).
Singh et al. Dried gamma-irradiation amniotic membrane as dressing in burn wound care. Journal of Tissue Viability 20:49-54 (2011).
Singh et al. Encyclopedia of Pharmaceutical Technology 2nd Ed. pp. 751-753 (2002).
Singh et al. Microbiological safety and clinical efficacy of radiation sterilized amniotic membranes for treatment of second-degree burns. Burns 33:505-510 (2007).
Solomon et al. Suppression of Interleukin 1a and interleukin 1b in human limbal epithelial cells cultured on the amniotic membrane stromal matrix. Br. J. Ophthalmol 85:444-449 (2001).
Sorsby. Amniotic Membrane Grafts in Burns. In: Modern Trends in Ophthalmology. Sorsby, A. ed. (NY: Paul B. Hoeber, Inc.), pp. 504-510 (1947).
Sorsby et al. Amniotic Membrane Grafts in Caustic Burns of the Eye (Burns of the Second Degree). Br. J. Ophthalmology 30:337-345 (1946).
Sorsby et al. Further Experience with Amniotic Membrane Grafts in Caustic Burns of the Eye. Br. J. Ophthalmology 31:409-418 (1947).
Sur et al. Anti-inflammatory and anti-platelet aggregation activity of human placental extract. Acta Pharmacol Sin 24(2):187-192 (2003).
Tan et al. Structural and Biological Comparison of Cryopreserved and Fresh Amniotic membrane Tissues. Journal Biomaterial and Tissue Engineering 4:379-388 (2014).
Taylor et al. Rate of Re-epithelialization Following Amniotic Membrane Transplantation. Invest. Ophthalmol. Vis. Sci. 39(4):S1038 (1998).
Temma et al. Effects of 4-hydroxy-2-nonenal, a marker of oxidative stress, on the cyclooxygenase-2 of human placenta in chorioamnionitis. Mol Hum Reprod 10(3):167-171 (2004).
Travis et al. Hyaluronan Enhances Contraction of Collagen by Smooth Muscle Cells and Adventitial Fibroblasts Role of CD44 and Implications for Constrictive Remodeling. Cir. Res. 88:77-83 (2001).
Trelford. The Amnion in Surgery, Past and Present. Am J. Obstet. Gynecol 134:833 (1979).
Tsai. Corneal Surfaces Reconstruction by Amniotic Membrane with Cultivated Autologous Limbo-Corneal Epithelium. Invest. Ophthalmol. Vis. Sci. 39(4):S429 (1998).
Tsai et al. Reconstruction of Damaged Corneas by Transplantation of Autologous Limbal Epithelial cells. New Eng. J. Med. 343(2):86-93 (2000).
Tseng et al. Amniotic Membrane Transplantation for Conjunctival Surface Reconstruction. Am. J. Ophthalmol. 124:765-774 (Dec. 1997).
Tseng et al. Down-regulation of TGF-β1, β2, β3 and TGF-β Receptor II Expression in Human Corneal Fibroblasts by Amniotic Membrane. Invest. Ophthalmol. Vis. Sci. 39(4):S428 (1998).
Tseng et al. How Does Amniotic Membrane Work? Ocular Surface J. 2(3):177-187 (2004).

(56) References Cited

OTHER PUBLICATIONS

Tseng et al. Suppression of Transforming Growth Factor-Beta Isoforms, TGF-β Receptor Type II, and Myofibroblast Differentiation in Cultured Human Corneal and Limbal Fibroblasts by Amniotic Membrane Matrix. J. Cell Physiol. 179:325-335 (1999).
Tsubota et al. Surgical Reconstruction of the Ocular Surface in Advanced Ocular Cicatricial Pemphigoid and Stevens-Johnson Syndrome. Am J Ophthalmology 122:38-52 (1996).
U.S. Appl. No. 11/528,902 Office Action dated Apr. 2, 2009.
U.S. Appl. No. 11/528,902 Office Action dated Dec. 16, 2009.
U.S. Appl. No. 11/528,902 Office Action dated Jan. 27, 2011.
U.S. Appl. No. 11/528,902 Office Action dated Sep. 8, 2010.
U.S. Appl. No. 11/528,980 Office Action dated Aug. 11, 2009.
U.S. Appl. No. 11/528,980 Office Action dated Jan. 10, 2011.
U.S. Appl. No. 11/528,980 Office Action dated Nov. 13, 2008.
U.S. Appl. No. 11/528,980 Office Action dated Oct. 15, 2010.
U.S. Appl. No. 11/529,658 Office Action dated Apr. 3, 2009.
U.S. Appl. No. 11/529,658 Office Action dated Dec. 16, 2009.
U.S. Appl. No. 11/529,658 Office Action dated Jan. 27, 2011.
U.S. Appl. No. 11/529,658 Office Action dated Sep. 3, 2010.
U.S. Appl. No. 11/535,924 Office Action dated Dec. 16, 2009.
U.S. Appl. No. 11/535,924 Office Action dated Jan. 31, 2011.
U.S. Appl. No. 11/535,924 Office Action dated Mar. 31, 2009.
U.S. Appl. No. 11/535,924 Office Action dated Sep. 8, 2010.
U.S. Appl. No. 13/322,896 Office Action dated Jan. 20, 2016.
U.S. Appl. No. 13/322,896 Office Action dated Jul. 6, 2015.
U.S. Appl. No. 13/322,896 Office Action dated Oct. 22, 2014.
U.S. Appl. No. 13/322,896 Office Action dated Oct. 4, 2016.
U.S. Appl. No. 13/322,896 Office Action dated Sep. 6, 2017.
U.S. Appl. No. 13/453,840 Office Action dated Aug. 21, 2012.
U.S. Appl. No. 13/704,231 Office Action dated Aug. 16, 2017.
U.S. Appl. No. 13/704,231 Office Action dated Aug. 2, 2016.
U.S. Appl. No. 13/704,231 Office Action dated Feb. 11, 2016.
U.S. Appl. No. 13/704,231 Office Action dated Jan. 19, 2017.
U.S. Appl. No. 13/704,231 Office Action dated Jun. 4, 2015.
U.S. Appl. No. 13/796,761 Office Action dated Dec. 9, 2014.
U.S. Appl. No. 13/802,204 Office Action dated Aug. 7, 2015.
U.S. Appl. No. 13/802,204 Office Action dated Feb. 26, 2015.
U.S. Appl. No. 13/802,204 Office Action dated Jan. 22, 2016.
U.S. Appl. No. 13/802,204 Office Action dated Jun. 15, 2018.
U.S. Appl. No. 13/802,204 Office Action dated Oct. 4, 2016.
U.S. Appl. No. 13/802,204 Office Action dated Sep. 7, 2017.
U.S. Appl. No. 13/802,264 Office Action dated Jul. 16, 2015.
U.S. Appl. No. 13/802,264 Office Action dated Nov. 28, 2014.
U.S. Appl. No. 13/802,359 Office Action dated Dec. 10, 2014.
U.S. Appl. No. 13/802,447 Office Action dated Dec. 15, 2014.
U.S. Appl. No. 14/004,992 Office Action dated Jun. 6, 2016.
U.S. Appl. No. 14/004,992 Office Action dated Nov. 23, 2015.
U.S. Appl. No. 14/848,143 Office Action dated Jun. 21, 2017.
U.S. Appl. No. 14/848,143 Office Action dated Oct. 20, 2016.
U.S. Appl. No. 14/848,148 Office Action dated Mar. 20, 2017.
U.S. Appl. No. 14/848,148 Office Action dated Oct. 28, 2016.
U.S. Appl. No. 14/848,153 Office Action dated Apr. 21, 2017.
U.S. Appl. No. 14/848,153 Office Action dated Oct. 25, 2016.
U.S. Appl. No. 14/880,135 Office Action dated Dec. 23, 2016.
U.S. Appl. No. 14/886,946 Office Action dated Apr. 18, 2016.
U.S. Appl. No. 14/886,946 Office Action dated Jan. 8, 2018.
U.S. Appl. No. 14/886,946 Office Action dated May 19, 2017.
U.S. Appl. No. 14/886,946 Office Action dated Oct. 5, 2016.
U.S. Appl. No. 14/886,946 Office Action dated Sep. 7, 2018.
U.S. Appl. No. 14/996,051 Office Action dated Apr. 2, 2018.
U.S. Appl. No. 14/996,051 Office Action dated Jul. 24, 2017.
U.S. Appl. No. 14/996,051 Office Action dated Sep. 7, 2018.
U.S. Appl. No. 15/195,189 Office Action dated May 30, 2018.
U.S. Appl. No. 15/215,228 Office Action dated May 30, 2018.
U.S. Appl. No. 15/348,736 Office Action dated Jan. 23, 2017.
U.S. Appl. No. 15/588,331 Office Action dated Apr. 2, 2018.
U.S. Appl. No. 15/636,227 Office Action dated Sep. 27, 2018.
Verbeek et al. Induction of alpha-smooth muscle actin expression in cultured human brain pericytes by transforming growth factor-beta 1. Am. J. Pathol. 144:372-382 (1994).
Wang et al. Corneal Haze is Reduced by Amniotic Membrane Matrix in Excimer Laser Photoablation in Rabbits. Invest Ophthalmol Vis Sci 38:S405 (1997).
Wisniewski et al. Cytokine-induced gene expression at the crossroads of innate immunity, inflammation and fertility: TSG-6 and PTX3/TSG-14. Cytokine Growth Factor Rev 15(2-3):129-146 (2004).
Wu et al. Wound healing effects of porcine placental extracts on rats with thermal injury. Br J Dermatol 148(2):236-245 (2003).
Yabushita et al. Clinicopathological Role of Serum-Derived Hyaluronan-Associated Protein (SHAP)-Hyaluronan Complex in Endometrial Cancer. Obstet Gynecol Inc. 2011:739150 (2011).
Yamaguchi et al. Negative regulation of transforming growth factor-β by the proteoglycan decorin. Nature 346(6281):281-284 (1990).
Yingsung et al. Molecular heterogeneity of the SHAP-hyaluronan complex. Isolation and characterization of the complex in synovial fluid from patients with rheumatoid arthritis. J Biol Chem 2878(35):32710-32718 (2003).
Yokomori et al. Advantages and Pitfalls of Amnion Inversion Repair for the Treatment of Large Unruptured Omphalocele: Results of 22 Cases. Journal of Pediatric Surgery 23:882-884 (1992).
Yoneda et al. Hyaluronic acid associated with the surfaces of cultured fibroblasts is linked to a serum-derived 85-kDa protein. J Biol Chem 265(9):5247-5257 (1990).
Yoshida. Placenta Power: For Health and Beauty—A useful guide for those seeking placenta-based remedies. Downloaded from http://www.melsmon.co.jp/img/commom/PlacentaPowerp002-121_04-09-08.pdf. (p. 1-41) (Aug. 2001).
Zhuo et al. SHAP potentiates the CD44-mediated leukocyte adhesion to the hyaluronan substratum. J Biol Chem 281(29):20303-20314 (2006).
U.S. Appl. No. 15/588,331 Office Action dated Aug. 6, 2019.
U.S. Appl. No. 14/886,946 Office Action dated May 28, 2019.
U.S. Appl. No. 14/996,051 Office Action dated May 28, 2019.
U.S. Appl. No. 15/879,042 Office Action dated Jul. 8, 2019.
Sood et al. Gene expression patterns in human placenta. PNAS 103(16):5478-5483 (2006).
U.S. Appl. No. 14/886,946 Office Action dated Oct. 25, 2019.
U.S. Appl. No. 14/996,051 Office Action dated Dec. 5, 2019.
U.S. Appl. No. 15/588,331 Office Action dated Mar. 2, 2021.
U.S. Appl. No. 15/588,331 Office Action dated Dec. 21, 2021.
U.S. Appl. No. 15/588,331 Office Action dated May 5, 2022.
Steed. Debridement. Am J Surg 187(5A):71S-74S (2014).
U.S. Appl. No. 14/886,946 Office Action dated Jan. 12, 2023.

\* cited by examiner

FETAL SUPPORT TISSUE PRODUCTS AND METHODS OF USE

CROSS REFERENCE TO RELATED APPLICATIONS

This application is a § 371 U.S. National Stage Entry of International Application No. PCT/US2017/015325 filed Jan. 27, 2017, which claims benefit of priority to U.S. Provisional Application No. 62/288,881, filed on Jan. 29, 2016, which are incorporated by reference herein in their entirety.

SUMMARY OF THE INVENTION

Disclosed herein, in certain embodiments, are methods of treating a complex wound in an individual in need thereof, comprising: administering to a complex wound in an individual, a therapeutically effective amount of a fetal support tissue product. In some embodiments, the complex wound is an ulcer, a lower extremity ulcer, a foot ulcer, a chronic foot ulcer, a pressure sore, or an ischemic wound. In some embodiments, the complex wound comprises exposed bone. In some embodiments, the complex wound comprises bone loss. In some embodiments, the method further comprises debriding the complex wound. In some embodiments, the debriding is surgical debridement. In some embodiments, the method further comprises resecting bone. In some embodiments, resecting the bone is performed until healthy bone is reached. In some embodiments, resecting the bone is performed to substantially remove necrotic or diseased bone. In some embodiments, the method further comprises opening the cortex of exposed bone. In some embodiments, the method further comprises administering a second fetal support tissue product to the complex wound. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof. In some embodiments, the method further comprises administering a treatment selected from the group consisting of antibiotics, hyperbaric oxygen therapy, revascularization therapy, and combinations thereof. In some embodiments, the individual has osteomyelitis. In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is ground, pulverized, morselized, a graft, a sheet a powder, a gel, a homogenate, or an extract. In some embodiments, the fetal support tissue product is aseptically processed or terminally-sterilized. In some embodiments, the fetal support tissue product is a graft. In some embodiments, the fetal support tissue product is a substantially-flattened sheet. In some embodiments, the fetal support tissue product is from human, non-human primate, cow, or pig. In some embodiments, the fetal support tissue product is an umbilical cord product. In some embodiments, the umbilical cord product comprises umbilical cord amniotic membrane. In some embodiments, the umbilical cord product comprises Wharton's Jelly. In some embodiments, the umbilical cord product is substantially free of blood. In some embodiments, the umbilical cord product lacks an umbilical cord vein and umbilical cord arteries.

Disclosed herein, in certain embodiments, are methods of treating a complex lower extremity ulcer in an individual in need thereof, comprising: administering to a complex lower extremity ulcer in the individual a therapeutically effective amount of a fetal support tissue product. In some embodiments, the method further comprises debriding the ulcer. In some embodiments, the debriding is surgical debridement. In some embodiments, the ulcer comprises exposed bone. In some embodiments, the ulcer comprises bone loss. In some embodiments, the ulcer comprises necrotic soft tissue, necrotic bone, or a combination thereof. In some embodiments, the method further comprises resecting the bone. In some embodiments, resecting the bone is performed until healthy bone is reached. In some embodiments, resecting the bone is performed to substantially remove necrotic or diseased bone. In some embodiments, the method further comprises opening the cortex of exposed bone. In some embodiments, the method further comprises administering a second fetal support tissue product to the ulcer. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof. In some embodiments, the method further comprises administering a treatment selected from the group consisting of antibiotics, hyperbaric oxygen therapy, revascularization therapy, and combinations thereof. In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is ground, pulverized, morselized, a graft, a sheet a powder, a gel, a homogenate, or an extract. In some embodiments, the fetal support tissue product is aseptically processed or terminally-sterilized. In some embodiments, the fetal support tissue product is a graft. In some embodiments, the fetal support tissue product is a substantially-flattened sheet. In some embodiments, the fetal support tissue product is from human, non-human primate, cow or pig. In some embodiments, the fetal support tissue product is an umbilical cord product. In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries.

Disclosed herein, in certain embodiments, are methods of repairing a spina bifida defect in an individual in need thereof, comprising: administering to a spina bifida defect in the individual a therapeutically effective amount of an umbilical cord product to repair the defect. In some embodiments, the individual is a fetus in utero. In some embodiments, the umbilical cord product is sutured in place. In some embodiments, the repair comprises regenerating epidermal, dermal, and subcutaneous layers. In some embodiments, the umbilical cord product is ground, pulverized, morselized, a graft, a sheet, a powder, a gel, a homogenate, or an extract. In some embodiments, the umbilical cord product is aseptically processed or terminally-sterilized. In some embodiments, the umbilical cord product is a graft. In some embodiments, the umbilical cord product is a substantially-flattened sheet. In some embodiments, the umbilical cord product is from human, non-human primate, cow or pig. In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries.

Disclosed herein, in certain embodiments, are methods of reducing or preventing scar formation from granulation tissue in an individual in need thereof, comprising: administering to granulation tissue in the individual a therapeutically effective amount of a fetal support tissue product thereby reducing or preventing scar formation. In some embodiments, the granulation tissue arises during healing of damaged tissue. In some embodiments, the damaged tissue is the result of a burn, a wound, an injury, an ulcer, or surgery. In some embodiments, the damaged tissue is skin, bone, muscle, tendon, cartilage, ligament, soft tissue, or a joint. In some embodiments, the method further comprises administering a second fetal support tissue product to the granulation tissue. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof. In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is ground, pulverized, morselized, a graft, a sheet, a powder, a gel, a homogenate, or an extract. In some embodiments, the fetal support tissue product is aseptically processed or terminally-sterilized. In some embodiments, the fetal support tissue product is a graft. In some embodiments, the fetal support tissue product is a substantially-flattened sheet. In some embodiments, the fetal support tissue product is from human, non-human primate, cow or pig. In some embodiments, the fetal support tissue product is an umbilical cord product. In some embodiments, the umbilical cord product comprises umbilical cord amniotic membrane. In some embodiments, the umbilical cord product comprises Wharton's Jelly. In some embodiments, the umbilical cord product is substantially free of blood. In some embodiments, the umbilical cord product lacks an umbilical cord vein and umbilical cord arteries.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates, for the 26 wounds that achieved complete healing, wounds separated into quartiles based on the initial wound area. FIG. 3B illustrates the total time to achieve complete wound closure for each respective quartile. Although there was a significant difference in the initial wound size, i.e., *$p<0.05$ vs. Q1; ˆ$p<0.05$ vs. Q2; #$p<0.05$ vs. Q3 (FIG. 3A), there is no difference in the mean time to achieve wound closure, $p>0.05$ when compared among the four quartiles (FIG. 3B).

DETAILED DESCRIPTION OF THE INVENTION

Figure 1:
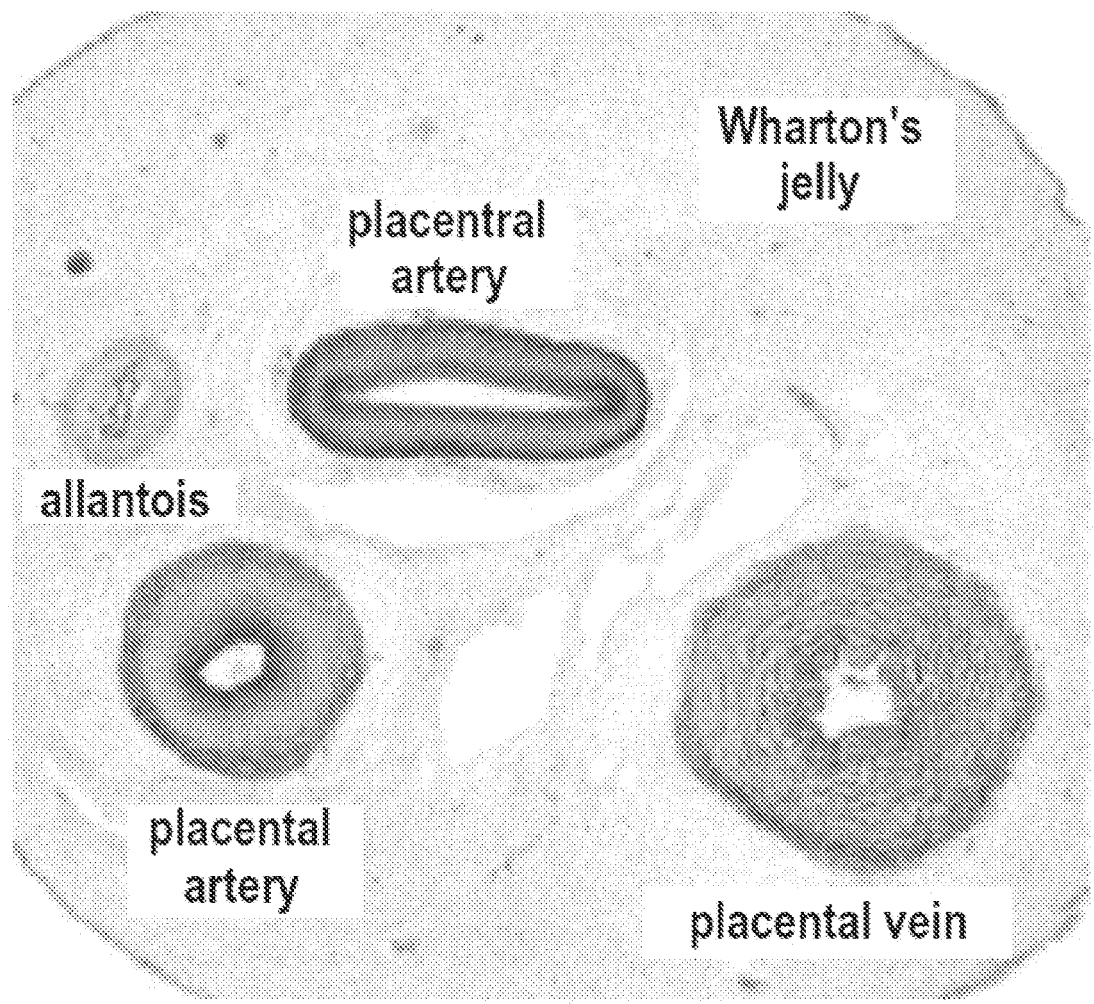
FIG. 1 exemplifies a cross-section of an umbilical cord (UC).

Provided herein are methods of treating complex wounds. Complex chronic wounds constitute life-threatening and severely debilitating conditions. Complex wounds may occur in patients requiring long periods of hospitalization with limited mobility for treating chronic illness (e.g., pressure sores or bed sores) and result in higher mortality and lower quality of life. Complex wounds due to venous stasis ulceration cause considerable morbidity and poor quality of life. Complex wounds may occur in patients having an autoimmune disease or under immunosuppressive therapy (e.g., vasculitis resulting in extensive ulcers) can cause longer hospitalization time and rising costs of treatment. Fournier's gangrene is another complex wound and is characterized by an infectious necrotizing fasciitis of the perineum and genital regions caused by a mixture of aerobic and anaerobic organisms. The mortality rate from this infection can be as high as 67%.

Non-healing diabetic foot ulcers (DFU), for example, have become a significant strain on healthcare systems around the world. The World Health Organization estimates that 347 million people worldwide suffer from diabetes and according to the US Centers of Disease Control, there were 25.8 million Americans in 2010 that have diabetes. Diabetic persons have approximately 25% risk of developing a foot ulcer in their lifetime with an estimated annual incidence rate of 2%.

Osteomyelitis and the exposure of bone and/or tendon, muscle, joint capsule are prevalent and serious complications of diabetic foot ulcers. Osteomyelitis refers to the inflammation or infection of the bone and is a condition that complicates approximately 20% of diabetic foot ulcers. Therefore, it is estimated that each year in the U.S., 100,000 people suffer from diabetic foot ulcers complicated by underlying osteomyelitis. Deep and large ulcers particularly those with exposed bone are more likely to be complicated by osteomyelitis. Nearly all diabetic foot ulcers with underlying osteomyelitis result from contiguous spread of infection from adjacent soft tissue to the cortical bone and/or bone marrow.

The prognosis of such complex non-healing diabetic foot ulcers is generally poor. Diabetic foot ulcers with exposed bone and with osteomyelitis are at high risk for delayed/non-healing of the ulcers, recurrence of ulcers and increased likelihood of amputation. Non-healing ulcers compromise the dermal first line of defense, making the patient to be susceptible to infection and non-infective tissue loss. Infection of the ulcer is often the event that prompts hospitalization and that leads to amputation. When the infection of the ulcer progresses to become severe or limb threatening, the amputation rate has been reported to be as high as 51%. Over 65,000 non-traumatic lower-limb amputations are performed in the U.S. for people with diabetes annually. The risk of amputation increases by four times when the foot ulcer is complicated by osteomyelitis compared to soft tissue infection alone. Unfortunately, after one major lower extremity amputation, the 5-year survival rate is estimated to be 50%, worse than those of most malignancies and second only to that of lung cancer. Moreover, once amputation occurs, 50% of the patients will develop an ulcer in the contralateral limb within 5 years. For amputation survivors, day-to-day functioning is greatly impaired. Many cannot walk, with or without the use of a cane or walker. A study found that in 2010, 22.8% of patients undergoing amputation of a lower extremity in the United States were readmitted to the hospital within 30 days, the highest rate of re-admission among the procedures considered in the study. Moreover, even with the best of medical care, amputation and its aftermath are traumatic experiences that can be expected to produce depression as the patient copes with the social and financial consequences of disfigurement and loss of function. Collectively, one can envision a grave picture of the seriousness of the complex non-healing foot ulcers of high risk that may lead to amputation in this country and worldwide.

The primary treatment goal of managing complex non-healing diabetic foot ulcers of high risk with a clinical suspicion of osteomyelitis that have exposed bone and/or tendon, muscle, joint capsule is to close the ulcer as expeditiously as possible, thereby reducing the risk of further wound related complications such as increased severity of infection that may lead to amputation. Current medical therapies include local wound care (e.g. wound dressing application and debridement), pain relief, pressure relief (off-loading) and treatment of infection. Additional new technologies have also been implemented such as vacuum extraction devices, hyperbaric oxygen treatment, and soundwave technology. New advances in wound care products include advanced skin substitutes and recombinant growth factors such as platelet-derived growth factor (PDGF). None of the advanced skin substitute products, however, are indicated for treating complex ulcers presenting with osteomyelitis. In addition, the vast majority have not been demonstrated to be safe or effective in the treatment of complex non-healing diabetic foot ulcers that have a depth exhibiting exposure of bone and/or tendon, muscle, joint capsule. At least some of these products are not indicated for ulcers with tendon, muscle, capsule or bone exposure, and are contraindicated for use on clinically infected wounds. Furthermore, nearly all of these advanced skin substitutes require "engraftment" or "graft take."

The presently claimed methods do not depend on the fetal support tissue product functioning as a scaffold and its engraftment depending on vascularization or host tissue/cell integration when applied on the wound bed. Hence, while not wishing to be bound by any particular theory, the fetal support tissue products (e.g., umbilical cord products) may employ a healing mechanism different from that of conventional advanced skin substitutes. In contrast to many of currently available therapies that are targeted to treat specific actions of a condition, for example, silver dressings are intended to specifically manage infection and PDGFs are intended to stimulate angiogenesis, the fetal support tissue products (e.g., umbilical cord products) exert multi-modal actions including anti-inflammatory, anti-scarring, and regenerative effects in different types of cells.

Complex wounds are often chronic and non-healing and provide additional treatment challenges when infection and necrotic tissue are present or occur in elderly or immunocompromised patients, or those having other chronic illnesses that contribute to poor healing (e.g., diabetes, immune system deficiency, arterial or venous insufficiency, chronic obstructive pulmonary disease, or paraplegia or quadriplegia). The present methods provide an improved treatment for complex wounds. As provided herein in a first exemplary study, 26 of 27 complex wounds were completely healed following administration of a fetal support tissue to the complex wound (Example 1). In a second exemplary study provided herein, a patient with a complex wound of the scalp involving tissue and bone necrosis following surgery and radiation therapy, treated with a fetal support tissue exhibited healing of the soft tissue and stimulation of bone regrowth. Thus, the presently disclosed methods address this serious and potentially fatal condition that has become a worldwide public health concern and presents a significant unmet medical need.

Disclosed herein, in certain embodiments, are methods of treating a complex wound in an individual in need thereof, comprising: applying a fetal support tissue product to a complex wound in the individual in an amount effective to treat the complex wound.

Disclosed herein, in certain embodiments, are methods of treating a complex lower extremity ulcer in an individual in need thereof, comprising: applying a fetal support tissue product to a complex lower extremity ulcer in the individual in an amount effective to treat the complex lower extremity ulcer.

Disclosed herein, in certain embodiments, are methods of repairing a spina bifida defect in an individual in need thereof, comprising: applying an umbilical cord product to a spina bifida defect in the individual in an amount effective to repair the defect.

Disclosed herein, in certain embodiments, are methods of reducing or preventing scar formation from granulation tissue in an individual in need thereof, comprising: applying a fetal support tissue product to granulation tissue in the individual in an amount effective to reduce or prevent scar formation.

Certain Definitions

As used herein, "fetal support tissue product" means any isolated product derived from tissue used to support the development of a fetus. Examples of fetal support tissue products include, but are not limited to, (i) placental amniotic membrane (PAM), or substantially isolated PAM, (ii) umbilical cord amniotic membrane (UCAM) or substantially isolated UCAM, (iii) chorion or substantially isolated chorion, (iv) amnion-chorion or substantially isolated amnion-chorion, (v) placenta or substantially isolated placenta, (vi) umbilical cord or substantially isolated umbilical cord, or (vii) any combinations thereof. In some embodiments, the fetal support tissue is selected from the group consisting of placental amniotic membrane (PAM), umbilical cord amniotic membrane (UCAM), chorion, amnion-chorion, placenta, umbilical cord, and any combinations thereof. In some embodiments, the fetal support tissue comprises umbilical cord. Fetal support tissue products include any form of the fetal support tissue, including cryopreserved, terminally-sterilized, lyophilized fetal support tissue or powders resulting from grinding fetal support tissue. In some embodiments, the fetal support tissue product is ground, pulverized, morselized, a graft, a sheet, a powder, a gel, a homogenate, an extract, or a terminally-sterilized product. In some embodiments, the fetal support tissue product is a graft.

As used herein, "human tissue" means any tissue derived from a human body. In some embodiments, the human tissue is a fetal support tissue selected from the group consisting of placental amniotic membrane, umbilical cord, umbilical cord amniotic membrane, chorion, amnion-chorion, placenta, or any combination thereof.

As used herein, the phrase "granulation tissue" refers to new tissue and tiny blood vessels that form on the surfaces of a wound during the healing process. In some embodiments, granulation tissue exhibits a bumpy or granular surface containing outgrowths of new capillaries. In some embodiments, granulation tissue grows from the base of a wound and is able to fill wounds of almost any size. In some embodiments, the fetal support tissue products disclosed herein are applied to granulation tissue to prevent or reduce the formation of scar tissue from the granulation tissue. In some embodiments, the fetal support tissue products disclosed herein are applied to granulation tissue to promote tissue regeneration wound repair. In some embodiments, hypergranulation prevents epithelization and the healing process is arrested.

As used herein, a "complex wound" refers to a wound that has exposed bone, muscle, tendon, joint capsule or a combination thereof. In some embodiments, the complex wound comprises exposed bone. In some embodiments, the complex wound comprises loss of bone. In some embodiments, bone loss is due to necrosis. In some embodiments, the complex wound includes necrosis of soft tissue, bone, or a combination thereof. Complex wounds are generally difficult to heal and highly susceptible to infection of the skin, muscle, and tendon, and predisposes the patient to a risk of osteomyelitis. Complex wounds are at greater risk of resulting in amputation, particularly when associated with ischemia or infection. In some embodiments, the complex wound is an ulcer, a lower extremity ulcer, a foot ulcer, a chronic foot ulcer, or an ischemic wound. In some embodiments, the complex wound is a pressure sore. In some embodiments, the complex wound is a venous stasis ulcer or an ulcer due to vasculitis. In some embodiments, the complex wound is ischemic. In some embodiments, the complex wound involves a wound of the scalp, skull, dura, or a combination thereof. In some embodiments, the complex wound is associated with infection. In some embodiments, the complex wound is associated with osteomyelitis. In some embodiments, the complex wound is ischemic and infected.

A "simple wound" as used herein refers to a wound of the skin with little or no damage to underlying tissues such as muscle, tendon, joint or bone.

As used herein, "graft" means a matrix of proteins (e.g., collagen and elastin) and glycans (e.g., dermatan, hyaluronan, and chondroitin) that is used to replace damaged, compromised, or missing tissue. In certain instances, the matrix is laid down and host cells gradually integrate into the matrix.

As used herein, "minimal manipulation" means (1) for structural tissue, processing that does not alter the original relevant characteristics of the tissue relating to the tissue's utility for reconstruction, repair, or replacement; and (2) for cells or nonstructural tissues, processing that does not alter the relevant biological characteristics of cells or tissues.

As used herein, "processing" means any activity performed on a fetal support tissue product, other than recovery, donor screening, donor testing, storage, labeling, packaging, or distribution, such as testing for microorganisms, preparation, sterilization, steps to inactivate or remove adventitious agents, preservation for storage, and removal from storage.

As used herein, "sheet" means any continuous expanse or surface. In some embodiments, a sheet of a fetal support tissue product is substantially flattened. In some embodiments, a sheet of a fetal support tissue product is flat. In some embodiments, a sheet of fetal support tissue product is tubular. The sheet can be any shape or size suitable for the wound to be treated. In some embodiments, the sheet is a square, circle, triangle, or rectangle.

As used herein, the term "subject" is used to mean any animal, preferably a mammal, including a human or non-human. The terms patient, subject, and individual are used interchangeably. None of the terms are to be interpreted as requiring the supervision of a medical professional (e.g., a doctor, nurse, physician's assistant, orderly, hospice worker).

"Substantially isolated" or "isolated" when used in the context of a fetal support tissue product means that the fetal support tissue product is separated from most other non-fetal support tissue materials (e.g., other tissues, red blood cells, veins, arteries) derived from the original source organism.

As used herein, the phrase "wherein the biological and structural integrity of the isolated fetal support tissue product is substantially preserved" means that when compared to the biological activity and structural integrity of fresh UC, the biological activity and structural integrity of the isolated UC has only decreased by about 5%, about 10%, about 15%, about 20%, about 25%, about 30%, about 35%, about 40%, about 50%, or about 60%.

The term "fresh fetal support tissue" refers to fetal support tissue that is less than 10 days old following birth, and which is in substantially the same form as it was following birth.

As used herein, "biological activity" means the activity of polypeptides and polysaccharides of the fetal support tissue. In some embodiments, the biological activity of polypeptides and polysaccharides found in fetal support tissue is anti-inflammatory, anti-scarring, anti-angiogenic, or anti-adhesion. In some embodiments, the biological activity is the biological activity of HC-HA/PTX3 complex in the fetal support tissue. In some embodiments, the biological activity of HC-HA/PTX3 complex in the fetal support tissue is substantially preserved. In some embodiments, the activity of polypeptides and polysaccharides found in fetal support tissue is promoting wound healing. In some embodiments, the activity of polypeptides and polysaccharides found in fetal support tissue is preventing scarring. In some embodiments, the activity of polypeptides and polysaccharides found in fetal support tissue is reducing inflammation.

As used herein, "structural integrity" means the integrity of stroma and basement membrane that make up the fetal support tissue product. In some embodiments, the structural integrity of the fetal support tissue product results in suture pull out strength.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. In some embodiments, treating a wound, such as a complex wound or complex lower extremity ulcer, refers to promoting wound closure. In some embodiments, treating a wound such as a complex wound or complex lower extremity ulcer refers to complete wound healing. In some embodiments, complete wound healing refers to 100% re-epithelialization of the wound area. In some embodiments, treating a wound, such as a complex wound or complex lower extremity ulcer, refers to promoting the generation new bone, tendon, muscle, and skin. In some embodiments, treating a wound, such as a complex wound or complex lower extremity ulcer, refers to promoting the generation of bone, tendon, muscle, and skin so that the wound is closed. In some embodiments, treating a wound, such as a complex wound or complex lower extremity ulcer, refers to avoiding or minimizing the need for amputation of an affected extremity.

Fetal Support Tissue Products

As used herein, the term "product" refers ground, pulverized, morselized, a graft, a sheet, a powder, a gel, a homogenate, an extract, or a terminally-sterilized product derived from a fetal support tissue. In some embodiments, the fetal support tissue product is a graft. In some embodiments, the fetal support tissue product is a sheet. In some embodiments, the fetal support tissue product is derived from placental amniotic membrane, umbilical cord, umbilical cord amniotic membrane, chorion, amnion-chorion, placenta, or any combination thereof.

In some embodiments, the fetal support tissue product is an umbilical cord product. In some embodiments, the umbilical cord product comprises umbilical cord amniotic membrane and at least some Wharton's jelly. In some embodiments, the umbilical cord product lacks umbilical cord vein and arteries.

As used herein, "placental amniotic membrane" (PAM) means amniotic membrane derived from the placenta. In some embodiments, the PAM is substantially isolated.

As used herein, "umbilical cord" means the organ that connects a developing fetus to the placenta. The umbilical cord is made up of amniotic membrane (UCAM), Wharton's Jelly, and blood vessels. The UCAM functions to regulate the fluid pressure within the UC. For a cross-sectional view of an umbilical cord, see FIG. 1. As used herein, "Wharton's Jelly" means a gelatinous substance within the umbilical cord, largely made up of mucopolysaccharides (hyaluronic acid and chondroitin sulfate). The umbilical cord further comprises two arteries (the umbilical arteries) and one vein (the umbilical vein), buried within the Wharton's jelly. In certain instances, an umbilical vein supplies a developing fetus with oxygenated blood from the placenta. In certain instances, an umbilical artery returns deoxygenated blood to the placenta.

As used herein, "umbilical cord amniotic membrane" (UCAM) means amniotic membrane derived from the umbilical cord. It reduces inflammation, reduces angiogenesis, reduces scarring, and reduces adhesion. UCAM is a translucent membrane. The UCAM has multiple layers: an epithelial layer; a basement membrane; a compact layer; a fibroblast layer; and a spongy layer. Further, the basement membrane of the UCAM serves as a natural niche for stem cells. It lacks blood vessels or a direct blood supply. In some embodiments, the UCAM is substantially isolated. In some embodiments, the UCAM further comprises Wharton's Jelly. In some embodiments, the UCAM further comprises at least a portion of Wharton's Jelly. In some embodiments, the UCAM comprises blood vessels and/or arteries. In some embodiments, the UCAM comprises Wharton's Jelly and blood vessels and/or arteries.

As used herein, "placenta" means the organ that connects a developing fetus to the maternal uterine wall to allow nutrient uptake, waste elimination, and gas exchange via the maternal blood supply. The placenta is composed of three layers. The innermost placental layer surrounding the fetus is called amnion. The allantois is the middle layer of the placenta (derived from the embryonic hindgut); blood vessels originating from the umbilicus traverse this membrane. The outermost layer of the placenta, the chorion, comes into contact with the endometrium. The chorion and allantois fuse to form the chorioallantoic membrane.

As used herein, "chorion" means the membrane formed by extraembryonic mesoderm and the two layers of trophoblast. The chorionic villi emerge from the chorion, invade the endometrium, and allow transfer of nutrients from maternal blood to fetal blood. The chorion consists of two layers: an outer layer formed by the trophoblast, and an inner layer formed by the somatic mesoderm; the amnion is in contact with the latter. The trophoblast is made up of an internal layer of cubical or prismatic cells, the cytotrophoblast or layer of Langhans, and an external layer of richly nucleated protoplasm devoid of cell boundaries, the syncytiotrophoblast. The avascular amnion is adherent to the inner layer of the chorion.

As used herein, "amnion-chorion" means a product comprising amnion and chorion. In some embodiments, the amnion and the chorion are not separated (i.e., the amnion is naturally adherent to the inner layer of the chorion). In some embodiments, the amnion is initially separated from the chorion and later combined with the chorion during processing.

Generation of UC Products

In some embodiments, the fetal support tissue products are UC products. In some embodiments, the UC products comprise: isolated UC tissue that does not comprise a vein or an artery. In some embodiments, the UC products comprise: isolated UC tissue that does not comprise a vein or an artery, a cell with metabolic activity, active HIV-1, active HIV-2, active HTLV-1, active hepatitis B, active hepatitis C, active West Nile Virus, active cytomegalovirus, active human transmissible spongiform encephalopathy, or active *Treponema pallidum*, wherein the natural structural integrity of the UC product is substantially preserved for at least 15 days after initial procurement. In some embodiments, the UC product comprises umbilical cord amniotic membrane and Wharton's Jelly. In some embodiments, the biological activity of HC-HA/PTX3 complex in the UC product is substantially preserved. In some embodiments, the biological activity of HC-HA/PTX3 complex in the UC product is substantially preserved for at least 15 days. In some embodiments, the biological and structural integrity of the UC product is substantially preserved for at least 20 days after initial procurement. In some embodiments, the biological and structural integrity of the UC product is substantially preserved for at least 25 days after initial procurement. In some embodiments, the biological and structural integrity of the UC product is substantially preserved for at least 30 days after initial procurement. In some embodiments, the biological and structural integrity of the UC product is substantially preserved for at least 35 days after initial procurement. In some embodiments, the biological and structural integrity of the UC product is substantially preserved for at least 40 days after initial procurement. In some embodiments, the biological and structural integrity of the UC product is substantially preserved for at least 45 days after initial procurement. In some embodiments, the biological and structural integrity of the UC product is substantially preserved for at least 50 days after initial procurement. In some embodiments, the biological and structural integrity of the UC product is substantially preserved for at least 55 days after initial procurement. In some embodiments, the biological and structural integrity of the UC product is substantially preserved for at least 60 days after initial procurement. In some embodiments, the biological and structural integrity of the UC product is substantially preserved for at least 90 days after initial procurement. In some embodiments, the biological and structural integrity of the UC product is substantially preserved for at least 180 days after initial procurement. In some embodiments, the biological and structural integrity of the UC product is substantially preserved for at least 1 year after initial procurement. In some embodiments, the biological and structural integrity of the UC product is substantially preserved for at least 2 years after initial procurement. In some embodiments, the biological and structural integrity of the UC product is substantially preserved for at least 3 years after initial procurement. In some embodiments, the biological and structural integrity of the UC product is substantially preserved for at least 4 years after initial procurement. In some embodiments, the biological and structural integrity of the UC product is substantially preserved for at least 5 years after initial procurement.

Further disclosed herein, in certain embodiments, a method of producing a UC product, comprising: obtaining pre-frozen umbilical cord, and removing the umbilical vein and umbilical arteries, wherein the structural integrity of the UC product is substantially preserved for at least 15 days after processing. In some embodiments, substantially all of the blood is removed from the umbilical cord product. In some embodiments, the umbilical cord is processed by thawing pre-frozen umbilical cord, removing the umbilical vein and umbilical arteries, and removing substantially all of the blood from the umbilical cord. In some embodiments, the biological and structural integrity of the UC product is substantially preserved for at least 20 days after processing. In some embodiments, the biological and structural integrity of the UC product is substantially preserved for at least 25 days after processing. In some embodiments, the biological and structural integrity of the UC product is substantially preserved for at least 30 days after processing. In some embodiments, the biological and structural integrity of the UC product is substantially preserved for at least 35 days after processing. In some embodiments, the biological and structural integrity of the UC product is substantially preserved for at least 40 days after processing. In some embodiments, the biological and structural integrity of the UC product is substantially preserved for at least 45 days after processing. In some embodiments, the biological and structural integrity of the UC product is substantially preserved for at least 50 days after processing. In some embodiments, the biological and structural integrity of the UC product is substantially preserved for at least 55 days after processing. In some embodiments, the biological and structural integrity of the UC product is substantially preserved for at least 60 days after processing. In some embodiments, the biological and structural integrity of the UC product is substantially preserved for at least 90 days after processing. In some embodiments, the biological and structural integrity of the UC product is substantially preserved for at least 180 days after processing. In some embodiments, the biological and structural integrity of the UC product is substantially preserved for at least 1 year after processing. In some embodiments, the biological and structural integrity of the UC product is substantially preserved for at least 2 years after processing. In some embodiments, the biological and structural integrity of the UC product is substantially preserved for at least 3 years after processing. In some embodiments, the biological and structural integrity of the UC product is substantially preserved for at least 4 years after processing. In some embodiments, the biological and structural integrity of the UC product is substantially preserved for at least 5 years after processing. In some embodiments, at least a portion of the Wharton's Jelly is removed. Umbilical cord is recovered from any suitable source (e.g., a hospital or tissue bank). In some embodiments, umbilical cord is obtained from a mammal. In some embodiments, umbilical cord is obtained from a human, a non-human primate, a cow or a pig.

The umbilical cord product is kept at −80° C. until donor and specimen eligibility has been determined. In some embodiments, storing the UC product at −80° C. kills substantially all cells found in the UC. In some embodiments, storing the UC product at −80° C. kills substantially all cells found in the UC product while maintaining or increasing the biological activity of the UC product (e.g., its anti-inflammatory, anti-scarring, anti-antigenic, and anti-adhesion properties) relative to fresh (i.e., non-frozen) UC. In some embodiments, storing the UC product at −80° C. results in the loss of metabolic activity in substantially all cells found in the UC. In some embodiments, storing the UC at −80° C. results in the loss of metabolic activity in substantially all cells found in the UC while maintaining or increasing the biological activity of the UCAM (e.g., its anti-inflammatory, anti-scarring, anti-antigenic, and anti-adhesion properties) relative to fresh (i.e., non-frozen) UC. In some embodiments, the UC is dried. In some embodiments, the UC is not dehydrated.

Processing of UC Products

All processing is done following Good Tissue Practices (GTP) to ensure that no contaminants are introduced into the UC product.

The umbilical cord is tested for HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* using FDA licensed screening test. Any indication that the tissue is contaminated with HIV-1, HIV-2, HTLV-1, hepatitis B and C, West Nile virus, or cytomegalovirus results in the immediate quarantine and subsequent destruction of the tissue specimen.

Further, the donor's medical records are examined for risk factors for and clinical evidence of hepatitis B, hepatitis C, or HIV infection. Any indication that the donor has risk factors for, and/or clinical evidence of, infection with HIV-1, HIV-2, HTLV-1, hepatitis B and C, West Nile virus, cytomegalovirus, human transmissible spongiform encephalopathy (e.g., Creutzfeldt-Jakob disease) and *Treponema pallidum* results in the immediate quarantine and subsequent destruction of the tissue specimen.

In some embodiments, the UC is frozen. In some embodiments, the UC is not frozen. If the UC is not frozen, it is processed as described below immediately.

In some embodiments, substantially all of the blood is removed from the UC (e.g., from any arteries and veins found in the UC, and blood that has infiltrated into the tissue). In some embodiments, substantially all of the blood is removed from the UC before the UC is frozen. In some embodiments, blood is not removed from the UC. In some embodiments, blood is not removed from the UC before the UC is frozen. In some embodiments, the blood is substantially removed after the UC has been frozen.

In some embodiments, the umbilical cord tissue is washed with buffer with agitation to remove excess blood and tissue. In some embodiments, the umbilical cord tissue is soaked with buffer with agitation to remove excess blood and tissue. In some embodiments, washing or soaking with agitation reduces the wash time. In some embodiments, the buffer wash solution is exchanged for fresh buffer solution. In some embodiments, the umbilical cord tissue is soaked in isotonic solution and the solution is exchanged. In some embodiments, the umbilical cord is washed with an isotonic buffer or tissue culture media. In some embodiments, the UC is washed with saline. In some embodiments, the UC is washed with PBS. In some embodiments, the UC is washed with 1×PBS. In some embodiments, the UC is washed with a TRIS-buffered saline. In some embodiments, the UC is washed with a HEPES-buffered saline. In some embodiments, the UC is washed with Ringer's solution. In some embodiments, the UC is washed with Hartmann's solution.

In some embodiments, the UC is washed with EBSS. In some embodiments, the UC is washed with HBSS. In some embodiments, the UC is washed with Tyrode's Salt Solution. In some embodiments, the UC is washed with Gey's Balanced Salt Solution. In some embodiments, the UC is washed with DMEM. In some embodiments, the UC is washed with EMEM. In some embodiments, the UC is washed with GMEM. In some embodiments, the UC is washed with RPMI.

In some embodiments, the UC is cut into multiple sections (e.g., using a scalpel). The size of the sections depends on the desired use of the UC product derived from the UC. In some embodiments, a section of the umbilical cord is cut longitudinally (e.g., using a scalpel or scissors) to open the UC. In some embodiments, the section of the UC is not cut into halves. In some embodiments, the section of the UC is cut into two halves. In some embodiments, additional cuts are made in the Wharton's Jelly to help flatten out the UC.

In some embodiments, the cut UC tissue is optionally washed again with buffer to further remove excess blood and tissue.

In some embodiments, the UC is fastened onto a substrate (e.g., a styrofoam board) using any suitable method (e.g., it is fastened with needles or pins (e.g., T pins)). In some embodiments, both ends of the umbilical cord are fastened to the substrate. In some embodiments, only one end is attached to the substrate. In some embodiments, the UC is stabilized with a substrate (e.g., absorbent towel cloth, drape). In some embodiments, the UC is oriented such that the inside face of the UC (e.g., the face comprising the Wharton's Jelly) is facing up while the outside face (i.e., the face comprising UCAM) is facing the substrate. If one end of the umbilical cord is left free, in some embodiments, the free end of the umbilical cord is held (e.g., with a clamp, hemostats or a set of forceps (e.g., wide serrated tip forceps)) while part or all of the Wharton's Jelly is removed. Alternatively, in some embodiments, both ends of the UC are left free.

The umbilical cord comprises two arteries (the umbilical arteries) and one vein (the umbilical vein). In some embodiments, the vein and arteries are removed from the UC. In certain instances, the vein and arteries are surrounded (or suspended or buried) within the Wharton's Jelly. In some embodiments, the vein and arteries are removed concurrently with the removal of the Wharton's Jelly. In some embodiments, the vein and arteries are peeled (or pulled) from the umbilical cord (e.g., using a set of forceps). In some embodiments, the vein and arteries are cut away (e.g., shaved) from the umbilical cord in sections. In some embodiments, a rotoblator removes the vein and arteries concurrently with the Wharton's Jelly. In some embodiments, a liposuction machine is utilized to remove the vein and arteries concurrently with the Wharton's Jelly. In some embodiments, a vein stripper is utilized to remove the vein and arteries concurrently with the Wharton's Jelly. In some embodiments, a liquid under high pressure removes the vein and arteries concurrently with the Wharton's Jelly. In some embodiments, a brush removes the vein and arteries concurrently with the Wharton's Jelly. In some embodiments, a surgical dermatome removes the vein and arteries concurrently with the Wharton's Jelly.

The desired thickness of the UC product determines how much of the Wharton's Jelly is removed. In some embodiments, the umbilical cord is contacted with a buffer to facilitate separation of the Wharton's Jelly and the UCAM. In some embodiments, the Wharton's Jelly is peeled from the UC in layers (e.g., using a set of forceps, hemostats). In some embodiments, the Wharton's Jelly is cut away (e.g., shaved) from the UC in sections. In some embodiments, a rotoblator (i.e., a catheter attached to a drill with a diamond coated burr) is utilized to remove the Wharton's Jelly. In some embodiments, a liposuction machine is utilized to remove the Wharton's Jelly. In some embodiments, a liquid under high pressure is applied to remove the Wharton's Jelly. In some embodiments, a brush is utilized to remove the Wharton's Jelly (e.g., a mechanized brush rotating under high speed). In some embodiments, a surgical dermatome is utilized to remove the Wharton's Jelly.

In some embodiments, the UC product comprises isolated umbilical cord amniotic membrane (UCAM). In certain instances, the UCAM comprises proteins, glycans, protein-glycan complexes (e.g., a complex of hyaluronic acid and a heavy chain of IαI and PTX3) and enzymes that promote tissue repair. For example, the stroma of UCAM contains growth factors, anti-angiogenic and anti-inflammatory proteins, as well as natural inhibitors to various proteases. In some embodiments, proteins and enzymes found in the UCAM diffuse out of the UC and into the surrounding tissue. In some embodiments, the UCAM is isolated by removing all of the Wharton's Jelly and umbilical vessels from the UC, leaving the UCAM. In some embodiments, the umbilical cord is contacted with a buffer to facilitate separation of the Wharton's Jelly and the UCAM. In some embodiments, the Wharton's Jelly is peeled from the UC in layers (e.g., using a set of forceps, hemostats). In some embodiments, the Wharton's Jelly is cut away (e.g., shaved) from the UC in sections. In some embodiments, a rotoblator (i.e., a catheter attached to a drill with a diamond coated burr) is utilized to remove the Wharton's Jelly. In some embodiments, a liposuction machine is utilized to remove the Wharton's Jelly. In some embodiments, a liquid under high pressure is applied to remove the Wharton's Jelly. In some embodiments, a brush is utilized to remove the Wharton's Jelly (e.g., a mechanized brush rotating under high speed). In some embodiments, a surgical dermatome is utilized to remove the Wharton's Jelly. In some embodiments, UCAM is removed directly from the tubular umbilical cord. In some embodiments, UCAM is shaved off of the umbilical cord. In some embodiments, UCAM is shaved off of the umbilical cord using any suitable method. In some embodiments, UCAM is shaved off of the umbilical cord using a shaver or a surgical dermatome. After substantially pure UCAM has been obtained, the UCAM is optionally washed with buffer to remove excess blood and tissue.

In some embodiments, the UC product comprises UCAM as a scaffold, and a plurality of cells integrated into the scaffold. In some embodiments, the cells are embryonic stem cells, mesenchymal stem cells or adult lineage-committed stem cells or differentiated epidermal cells (e.g., to treat a burn or a surgical incision in the skin). In some embodiments, the cells are mesothelial cells (e.g., to treat to a wound (e.g., surgical incision) in an internal organ).

In some embodiments, the use is a homologous use (e.g., a functional homologous use or a structural homologous use). In some embodiments, the UC product is minimally manipulated. In some embodiments, the UC product does not comprise another article, except for water, crystalloids, or a sterilizing, preserving, or storage agent. In some embodiments, the UC product does not have a systemic effect and is not dependent upon the metabolic activity of living cells for its primary function.

In some embodiments, the UC products are in any suitable shape (e.g., a square, a circle, a triangle, a rectangle). In some embodiments, the UC product is generated from a sheet of UC. In some embodiments, the sheet is flat. In some embodiments, the sheet is tubular.

The size of the UC product depends on the desired use of the UC product. In some embodiments, the UC product is cut into multiple sections (e.g., using a scalpel). In some embodiments, the UC product is divided into sections that are about 1.0 cm×about 0.25 cm. In some embodiments, the UC product is divided into sections that are about 1.0 cm×about 0.5 cm. In some embodiments, the UC product is divided into sections that are about 1.0 cm×about 0.75 cm. In some embodiments, the UC product is divided into sections that are about 1 cm×about 1 cm. In some embodiments, the UC product is divided into sections that are about 1 cm×about 2 cm. In some embodiments, the UC product is divided into sections that are about 1 cm×about 3 cm. In some embodiments, the UC product is divided into sections that are about 1 cm×about 4 cm. In some embodiments, the UC product is divided into sections that are about 1 cm×about 5 cm. In some embodiments, the UC product is divided into sections that are about 1 cm×about 6 cm. In some embodiments, the UC product is divided into sections that are about 2 cm×about 2 cm. In some embodiments, the UC product is divided into sections that are about 2 cm×about 3 cm. In some embodiments, the UC product is divided into sections that are about 2 cm×about 4 cm. In some embodiments, the UC product is divided into sections that are about 2 cm×about 5 cm. In some embodiments, the UC product is divided into sections that are about 2 cm×about 6 cm. In some embodiments, the UC product is divided into sections that are about 3 cm×about 3 cm. In some embodiments, the UC product is divided into sections that are about 3 cm×about 4 cm. In some embodiments, the UC product is divided into sections that are about 3 cm×about 5 cm. In some embodiments, the UC product is divided into sections that are about 3 cm×about 6 cm. In some embodiments, the UC product is divided into sections that are about 4 cm×about 4 cm. In some embodiments, the UC product is divided into sections that are about 4 cm×about 5 cm. In some embodiments, the UC product is divided into sections that are about 4 cm×about 6 cm. In some embodiments, the UC product is divided into sections that are about 5 cm×about 5 cm. In some embodiments, the UC product is divided into sections that are about 5 cm×about 6 cm. In some embodiments, the UC product is divided into sections that are about 6 cm×about 6 cm. In some embodiments, the UC product is divided into sections that are about 8 cm×about 1 cm. In some embodiments, the UC product is divided into sections that are about 8 cm×about 2 cm. In some embodiments, the UC product is divided into sections that are about 8 cm×about 3 cm. In some embodiments, the UC product is divided into sections that are about 8 cm×about 4 cm. In some embodiments, the UC product is divided into sections that are about 8 cm×about 5 cm. In some embodiments, the UC product is divided into sections that are about 8 cm×about 6 cm. In some embodiments, the UC product is divided into sections that are about 10 cm×about 10 cm. In some embodiments, the UC product is divided into sections that are about 12 cm×about 10 cm. In some embodiments, the UC product is divided into sections that are about 15 cm×about 10 cm. In some embodiments, the UC product is divided into sections that are about 20 cm×about 10 cm. In some embodiments, the UC product is divided into sections that are about 25 cm×about 10 cm. In some embodiments, the UC product is divided into sections that are about 30 cm×about 10 cm.

In some embodiments, the UC product is contacted with a buffer to remove substantially all remaining red blood cells. In some embodiments, the UC product is contacted with an isotonic buffer. In some embodiments, the UC product is contacted with saline. In some embodiments, the UC product is contacted with PBS. In some embodiments, the UC product is contacted with PBS 1×. In some embodiments, the UC product is contacted with Ringer's solution. In some embodiments, the UC product is contacted with Hartmann's solution. In some embodiments, the UC product is contacted with a TRIS-buffered saline. In some embodiments, the UC product is contacted with a HEPES-buffered saline. In some embodiments, the UC product is contacted with EBSS. In some embodiments, the UC product is contacted with HBSS. In some embodiments, the UC product is contacted with Tyrode's salt Solution. In some embodiments, the UC product is contacted with Gey's Balanced Salt Solution. In some embodiments, the UC product is contacted with DMEM. In some embodiments, the UC product is contacted with EMEM. In some embodiments, the UC product is contacted with GMEM. In some embodiments, the UC product is contacted with RPMI.

In some embodiments, the UC product is contacted with buffer under agitation to remove substantially all remaining red blood cells. In some embodiments, the UC product is contacted with a buffer for 10 minutes. In some embodiments, the UC product is contacted with a buffer for 15 minutes. In some embodiments, the UC product is contacted with a buffer for 20 minutes. In some embodiments, the UC product is contacted with a buffer for 25 minutes. In some embodiments, the UC product is contacted with a buffer for 30 minutes. In some embodiments, the UC product is contacted with a buffer for 35 minutes. In some embodiments, the UC product is contacted with a buffer for 40 minutes. In some embodiments, the UC product is contacted with a buffer for 45 minutes. In some embodiments, the UC product is contacted with a buffer for 50 minutes. In some embodiments, the UC product is contacted with a buffer for 55 minutes. In some embodiments, the UC product is contacted with a buffer for 60 minutes. In some embodiments, the UC product is contacted with a buffer for 2 hours. In some embodiments, the UC product is contacted with a buffer for 3 hours. In some embodiments, the UC product is contacted with a buffer for 4 hours. In some embodiments, the UC product is contacted with a buffer for 5 hours. In some embodiments, the UC product is contacted with a buffer for 6 hours. In some embodiments, the UC product is contacted with a buffer for 6 hours. In some embodiments, the UC product is contacted with a buffer for 10 hours. In some embodiments, the UC product is contacted with a buffer for 12 hours. In some embodiments, the UC product is contacted with a buffer for 18 hours. In some embodiments, the UC product is contacted with a buffer for 24 hours. In some embodiments, the UC product is contacted with a buffer for 2 days. In some embodiments, the UC product is contacted with a buffer for 3 days. In some embodiments, the UC product is contacted with a buffer for 4 days. In some embodiments, the UC product is contacted with a buffer for 5 days. In some embodiments, the UC product is contacted with a buffer for 6 days. In some embodiments, the UC product is contacted with a buffer for 7 days. In some embodiments, the UC product is contacted with a buffer for 10 days. In some embodiments, the UC product is contacted with a buffer for 14 days. In some embodiments, the UC product is contacted with a buffer for 21 days. In some embodiments, the UC product is contacted with a buffer for 30 days. In some embodiments, the buffer is optionally changed during the contacting (e.g., when the rate at which red blood cells diffuse from the UC sheets slows). In some embodiments, a magnetic stirrer is added during the contacting. In some embodiments, adding (and activating) a magnetic stirrer increases the rate at which the red blood cells diffuse from the UC sheets.

Processing to Generate Pulverized Fetal Support Tissue Product

In some embodiments, isolated fetal support tissue product is used to generate a pulverized fetal support tissue product. As used herein, "pulverized fetal support tissue product" means a fetal support tissue product comprising tissue that has been broken up (or, disassociated). In some embodiments, the pulverized fetal support tissue product is a dry powder. In some embodiments, the pulverized fetal support tissue product is further processed into a solution, suspension or emulsion by mixing the fetal support tissue powder with a carrier. In some embodiments, the pulverized fetal support tissue product is formulated into a cream, lotion, ointment, paste, gel, film or paint. In some embodiments, the pulverized fetal support tissue product is contacted with a patch or wound dressing.

In some embodiments, the isolated fetal support tissue is pulverized by any suitable method. In some embodiments, the isolated fetal support tissue is pulverized by use of a pulverizer (e.g., a Bessman Tissue Pulverizer, a Biospec biopulverizer, or a Covaris CryoPrep). In some embodiments, the isolated fetal support tissue is pulverized by use of a tissue grinder (e.g., a Potter-Elvehjem grinder or a Wheaton Overhead Stirrer). In some embodiments, the isolated fetal support tissue is pulverized by use of a sonicator. In some embodiments, the isolated fetal support tissue is pulverized by use of a bead beater. In some embodiments, the isolated fetal support tissue is pulverized by use of a freezer/mill (e.g., a SPEX SamplePrep Freezer/Mill or a Retch Ball Mill). In some embodiments, the isolated fetal support tissue is pulverized by use of a pestle and mortar. In some embodiments, the isolated fetal support tissue is pulverized by manual use of a pestle and mortar.

In some embodiments, the isolated fetal support tissue is optionally lyophilized before being pulverized. In some embodiments, the isolated fetal support tissue is lyophilized by any suitable method (e.g., exposure to a liquid gas, placement in a freezer). In some embodiments, the isolated fetal support tissue is placed in the vacuum chamber of a lyophilization device until all or substantially all fluid (e.g., water) has been removed. In some embodiments, the isolated fetal support tissue is lyophilized following freezing (e.g., exposure to a temperature below 0° C., −20° C., −40° C., −50° C., −60° C., −70° C., −75° C., −80° C., −90° C., or −100° C.).

Storage of the Fetal Support Tissue Product

In some embodiments, the fetal support tissue product is stored for later use. In some embodiments, storing the fetal support tissue product does not destroy the integrity of the fetal support tissue extracellular matrix. In some embodiments, the fetal support tissue product is lyophilized. In some embodiments, the fetal support tissue product is stored in any suitable storage medium. In some embodiments, the fetal support tissue product is stored in 50% DMEM+50% Glycerol. In some embodiments, the fetal support tissue product is stored in 10%, 20%, 30%, 40%, 50%, 60%, 70%, 80%, 90% or 100% glycerol. In some embodiments, the fetal support tissue product is stored in 10%, 20%, 30%, 40%, 50%, 60%, 70%, 80%, 90% or 100% propylene glycol.

In some embodiments, the fetal support tissue product is optionally contacted with a substrate (i.e., a supportive backing). In some embodiments, the fetal support tissue product is not contacted with a substrate. In some embodiments, the fetal support tissue product is orientated such that the fetal support tissue product is in contact with the substrate. In some embodiments, the fetal support tissue product is orientated such that the stroma is in contact with the substrate. In some embodiments the fetal support tissue product is orientated such that the epithelial side is in contact with the substrate.

In some embodiments, the fetal support tissue product is attached to the substrate. In some embodiments, the substrate is nitrocellulose paper (NC). In some embodiments, the substrate is nylon membrane (NM). In some embodiments, the substrate is polyethersulfone membrane (PES).

Cryopreservation

In some embodiments, the fetal support tissue product is frozen for cryopreservation. In some embodiments, cryopreserving the fetal support tissue product does not destroy the integrity of the fetal support tissue extracellular matrix. In some embodiments, the fetal support tissue product is exposed to a liquid gas (e.g., liquid nitrogen or liquid hydrogen). In some embodiments, the fetal support tissue product is exposed to liquid nitrogen. In some embodiments, the fetal support tissue product does not contact the liquid gas. In some embodiments, the fetal support tissue product is placed in a container and the container is contacted with liquid gas. In some embodiments, the fetal support tissue product is exposed to the liquid gas until the fetal support tissue product is frozen.

Lyophilization

In some embodiments, the fetal support tissue product is lyophilized. In some embodiments, the fetal support tissue product is lyophilized following freezing. In some embodiments, the fetal support tissue product is lyophilized following freezing by any suitable method (e.g., exposure to a liquid gas, placement in a freezer). In some embodiments, the fetal support tissue product is frozen by exposure to a temperature below about 0° C. In some embodiments, the fetal support tissue product is frozen by exposure to a temperature below about −20° C. In some embodiments, the fetal support tissue product is frozen by exposure to a temperature below about −40° C. In some embodiments, the fetal support tissue product is frozen by exposure to a temperature below about −50° C. In some embodiments, the fetal support tissue product is frozen by exposure to a temperature below about −60° C. In some embodiments, the fetal support tissue product is frozen by exposure to a temperature below about −70° C. In some embodiments, the fetal support tissue product is frozen by exposure to a temperature below about −75° C. In some embodiments, the fetal support tissue product is frozen by exposure to a temperature below about −80° C. In some embodiments, the fetal support tissue product is frozen by exposure to a temperature below about −90° C. In some embodiments, the fetal support tissue product is frozen by exposure to a temperature below about −100° C. In some embodiments, the fetal support tissue product is frozen by exposure to a liquid gas.

In some embodiments, the cryopreserved fetal support tissue product is lyophilized. In some embodiments, the cryopreserved fetal support tissue product is placed in the vacuum chamber of a lyophilization device until all or substantially all fluid (e.g., water) has been removed.

Sterilization

In some embodiments, the fetal support tissue product is subject to terminal sterilization by any suitable (e.g., medically acceptable) method. In some embodiments, the lyophilized fetal support tissue product is exposed to gamma radiation for a period of time sufficient to sterilize the fetal support tissue product. In some embodiments, the lyophilized fetal support tissue product is exposed to gamma radiation at 25 kGy for a period of time sufficient to sterilize the fetal support tissue product. In some embodiments, the lyophilized fetal support tissue product is exposed to an electron beam for a period of time sufficient to sterilize the fetal support tissue product. In some embodiments, the lyophilized fetal support tissue product is exposed to X-ray radiation for a period of time sufficient to sterilize the fetal support tissue product. In some embodiments, the lyophilized fetal support tissue product is exposed to UV radiation for a period of time sufficient to sterilize the fetal support tissue product.

Rehydration

In some embodiments, the fetal support tissue product is partially or fully rehydrated. In some embodiments, the fetal support tissue product is rehydrated by contacting the fetal support tissue product with a buffer or with water. In some embodiments, the fetal support tissue product is contacted with an isotonic buffer. In some embodiments, the fetal support tissue is contacted with saline. In some embodiments, the fetal support tissue product is contacted with PBS. In some embodiments, the fetal support tissue product is contacted with Ringer's solution. In some embodiments, the fetal support tissue product is contacted with Hartmann's solution. In some embodiments, the fetal support tissue product is contacted with a TRIS-buffered saline. In some embodiments, the fetal support tissue product is contacted with a HEPES-buffered saline; 50% DMEM+50% Glycerol; 10%, 20%, 30%, 40%, 50%, 60%, 70%, 80%, 90% or 100% glycerol; and/or 10%, 20%, 30%, 40%, 50%, 60%, 70%, 80%, 90% or 100% propylene glycol.

In some embodiments, the fetal support tissue product is contacted with a buffer for 10 minutes. In some embodiments, the fetal support tissue product is contacted with a buffer for 15 minutes. In some embodiments, the fetal support tissue product is contacted with a buffer for 20 minutes. In some embodiments, the fetal support tissue product is contacted with a buffer for 25 minutes. In some embodiments, the fetal support tissue product is contacted with a buffer for 30 minutes. In some embodiments, the fetal support tissue product is contacted with a buffer for 35 minutes. In some embodiments, the fetal support tissue product is contacted with a buffer for 40 minutes. In some embodiments, the fetal support tissue product is contacted with a buffer for 45 minutes. In some embodiments, the fetal support tissue product is contacted with a buffer for 50 minutes. In some embodiments, the fetal support tissue product is contacted with a buffer for 55 minutes. In some embodiments, the fetal support tissue product is contacted with a buffer for 60 minutes. In some embodiments, the fetal support tissue product is contacted with a buffer for 2 hours. In some embodiments, the fetal support tissue product is contacted with a buffer for 3 hours. In some embodiments, the fetal support tissue product is contacted with a buffer for 4 hours. In some embodiments, the fetal support tissue product is contacted with a buffer for 5 hours. In some embodiments, the fetal support tissue product is contacted with a buffer for 6 hours. In some embodiments, the fetal support tissue product is contacted with a buffer for 6 hours. In some embodiments, the fetal support tissue product is contacted with a buffer for 10 hours. In some embodiments, the fetal support tissue product is contacted with a buffer for 12 hours. In some embodiments, the fetal support tissue product is contacted with a buffer for 18 hours. In some embodiments, the fetal support tissue product is contacted with a buffer for 24 hours.

Methods of Use

Treating Complex Wounds

Disclosed herein, in certain embodiments, are methods of treating a complex wound in an individual in need thereof, comprising: administering to a complex wound in the individual a therapeutically effective amount of a fetal support tissue product. In some embodiments, the complex wound is an ulcer, a lower extremity ulcer, a foot ulcer, a chronic foot ulcer, or an ischemic wound. In some embodiments, the complex wound is a wound of the scalp, skull, dura, or combination thereof. In some embodiments, the complex wound comprises exposed bone. In some embodiments, the complex wound is ischemic. In some embodiments, the complex wound is infected. In some embodiments, the complex wound is ischemic and infected. In some embodiments, the method further comprises debriding the complex wound. In some embodiments, the debriding is surgical debridement. In some embodiments, the method further comprises resecting bone. In some embodiments, the resecting the bone is performed until healthy bone is reached. In some embodiments, the resecting the bone is performed to substantially remove necrotic or diseased bone. In some embodiments, the method further comprises opening the cortex of exposed bone. In some embodiments, the opening the cortex comprises making holes in the cortical bone to the trabecular bone. In some embodiments, the method further comprises monitoring healing of the wound. In some embodiments, the method further comprises administering a second fetal support tissue product to the wound. In some embodiments, the method further comprises administering a second fetal support tissue product to the exposed bone. In some embodiments, administering a second fetal support tissue product to the exposed bone comprises injecting the second fetal support tissue into the exposed bone. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof. In some embodiments, the method further comprising administering a treatment selected from the group consisting of antibiotics, hyperbaric oxygen therapy, revascularization therapy, and combinations thereof. In some embodiments, the individual has osteomyelitis. In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is derived umbilical cord. In some embodiments, the fetal support tissue product is ground, pulverized, morselized, a graft, a powder, a gel, a homogenate, an extract, or a terminally-sterilized product. In some embodiments, the fetal support tissue product is a graft. In some embodiments, the fetal support tissue product is a substantially-flattened sheet. In some embodiments, the fetal support tissue product is from human, non-human primate, cow or pig. In some embodiments, the fetal support tissue product is substantially free of blood.

In some embodiments, the fetal support tissue product is an umbilical cord product. In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries. In some embodiments, the umbilical cord product is ground, pulverized, morselized, a graft, a powder, a gel, a homogenate, or an extract. In some embodiments, the umbilical cord product is a graft. In some embodiments, the umbilical cord product is a substantially-flattened sheet. In some embodiments, the umbilical cord product is from human umbilical cord, non-human primate umbilical cord, cow umbilical cord or pig umbilical cord.

Treating Complex Lower Extremity Ulcer

Disclosed herein, in certain embodiments, are methods of treating a complex lower extremity ulcer in an individual in need thereof, comprising: administering to a complex lower extremity ulcer in the individual a therapeutically effective amount of a fetal support tissue product to treat the complex lower extremity ulcer. In some embodiments, the ulcer is a foot ulcer, a chronic ulcer, a diabetic foot ulcer, an arterial insufficiency ulcer, a venous stasis (VS) ulcer, a neurotrophic ulcer, or an arterial (ischemic) ulcer. In some embodiments, the complex wound comprises exposed bone. In some embodiments, the method further comprises debriding the ulcer. In some embodiments, the debriding is surgical debridement. In some embodiments, the method further comprises resecting the bone. In some embodiments, the resecting the bone is performed until healthy bone is reached. In some embodiments, the resecting the bone is performed to substantially remove necrotic or diseased bone. In some embodiments, the method further comprises opening the cortex of exposed bone. In some embodiments, the opening the cortex comprises making holes in the cortical bone to the trabecular bone. In some embodiments, the method further comprises monitoring healing of the ulcer. In some embodiments, the method further comprises administering a second fetal support tissue product to the ulcer. In some embodiments, the method further comprises administering a second fetal support tissue product to the exposed bone. In some embodiments, administering a second fetal support tissue product to the exposed bone comprises injecting the second fetal support tissue into the exposed bone. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof. In some embodiments, the method further comprises administering a treatment selected from the group consisting of antibiotics, hyperbaric oxygen therapy, revascularization therapy, and combinations thereof. In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is derived umbilical cord. In some embodiments, the fetal support tissue product is ground, pulverized, morselized, a graft, a powder, a gel, a homogenate, an extract, or a terminally-sterilized product. In some embodiments, the fetal support tissue product is a graft. In some embodiments, the fetal support tissue product is a substantially-flattened sheet. In some embodiments, the fetal support tissue product is from human, non-human primate, cow or pig. In some embodiments, the fetal support tissue product is substantially free of blood.

In some embodiments, the fetal support tissue product is an umbilical cord product. In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries. In some embodiments, the umbilical cord product is ground, pulverized, morselized, a graft, a powder, a gel, a homogenate, or an extract. In some embodiments, the umbilical cord product is a graft. In some embodiments, the umbilical cord product is a substantially-flattened sheet. In some embodiments, the umbilical cord product is from human umbilical cord, non-human primate umbilical cord, cow umbilical cord or pig umbilical cord.

Treating Spina Bifida

Spina bifida is a birth defect of the neural tube involving incomplete closing of the backbone and the membranes around the spinal cord. Spina bifida can be classified as spina bifida occulta or spina bifida cystica. Spina bifida occulta is the mildest form of spina bifida in which one or more vertebrae fail to properly form, and usually only visibly manifests as a dimple, tuft of hair, or red mark on the back. Spina bifida cystica is a more severe form and takes the form of either a cyst containing meninges (meningocele), a cyst containing both meninges and spinal cord (meningomyelocele) or only spinal cord (myleocele, also known as myeloschisis).

Disclosed herein, in certain embodiments, are methods of repairing a spina bifida defect in an individual in need thereof comprising administering to a spina bifida defect in the individual a therapeutically effective amount of an umbilical cord product to repair the defect. In some embodiments, the spina bifida defect is spina bifida cystica defect. In some embodiments, the spina bifida cystica defect is a meningocele defect, a meningomylocele defect, or a myeocele defect. In some embodiments, the individual is a fetus in utero or a neonate. In some embodiments, the individual is a fetus in utero. In some embodiments, the umbilical cord product is sutured in place. In some embodiments, the repair comprises regenerating epidermal, dermal, and subcutaneous layers. In some embodiments, the administering an umbilical cord product comprises in utero surgery. In some embodiments, the administering an umbilical cord product comprises surgery carried out within 12, 24, or 48 hours after birth.

In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries. In some embodiments, the umbilical cord product is ground, pulverized, morselized, a graft, a sheet, a powder, a gel, a homogenate, or an extract. In some embodiments, the umbilical cord product is a graft. In some embodiments, the umbilical cord product is a substantially-flattened sheet. In some embodiments, the umbilical cord product is aseptically processed or terminally-sterilized. In some embodiments, the umbilical cord product is from human umbilical cord, non-human primate umbilical cord, cow umbilical cord or pig umbilical cord.

Reducing or Preventing Scar Formation from Granulation Tissue

Disclosed herein, in certain embodiments, are methods of reducing or preventing scar formation from granulation tissue in an individual in need thereof, comprising: administering to granulation tissue in the individual a therapeutically effective amount of a fetal support tissue product to reduce or prevent scar formation. In some embodiments, the granulation tissue arises during healing of damaged tissue. In some embodiments, the damaged tissue is the result of a burn, a wound, an injury, an ulcer, or surgery. In some embodiments, damaged tissue is skin, bone, muscle, tendon, cartilage, ligament, soft tissue, or a joint. In some embodiments, the method further comprises monitoring healing of the damaged tissue. In some embodiments, the method further comprises administering a second fetal support tissue product to the granulation tissue. In some embodiments, the method further comprises covering the fetal support tissue product with a dressing, antimicrobial dressing, antimicrobial alginate dressing, compression dressing, metipel wound contact layer, gauze, patch, substrate, backing, covering, bandage, or a combination thereof.

In some embodiments, the fetal support tissue product is derived from placental amniotic membrane, umbilical cord, umbilical cord amniotic membrane, chorion, amnion-chorion, placenta, or any combination thereof. In some embodiments, the fetal support tissue product is ground, pulverized, morselized, a graft, a powder, a gel, a homogenate, an extract, or a terminally-sterilized product. In some embodiments, the fetal support tissue product is a graft. In some embodiments, the fetal support tissue product is a substantially-flattened sheet. In some embodiments, the fetal support tissue product is from human, non-human primate, cow or pig. In some embodiments, the fetal support tissue product is substantially free of blood.

In some embodiments, the fetal support tissue product is an umbilical cord product. In some embodiments, the umbilical cord product comprises umbilical cord amniotic membrane. In some embodiments, the umbilical cord product further comprises Wharton's Jelly. In some embodiments, the umbilical cord product is substantially free of blood. In some embodiments, the umbilical cord product lacks an umbilical cord vein and umbilical cord arteries. In some embodiments, the umbilical cord product is ground, pulverized, morselized, a graft, a powder, a gel, a homogenate, or an extract. In some embodiments, the umbilical cord product is a graft. In some embodiments, the umbilical cord product is a substantially-flattened sheet. In some embodiments, the umbilical cord product is from human umbilical cord, non-human primate umbilical cord, cow umbilical cord or pig umbilical cord.

EXAMPLES

Example 1

A Single Center, Retrospective Study of Cryopreserved Umbilical Cord to Promote Healing of Complex Foot Ulcers in Patients with Underlying Osteomyelitis A retrospective review was performed to assess healing of 31 patients presenting with 33 complex foot ulcers with a confirmed histopathological diagnosis of osteomyelitis treated by the same surgeon at a single wound care center by sharp debridement, resection of affected bone, open cortex and application of cryopreserved umbilical cord (cUC).
Methods
Clinical Data Retrieval This retrospective review was conducted after approval by the Institutional Review Board of the Barnabas Health System (West Orange, N.J.) to capture, verify, and subsequently analyze all relevant clinical data on 31 eligible patients that had been managed by the same surgeon between January 2013 and December 2014 at the Wound Care Center at Clara Maass Medical Center to determine the safety and effectiveness of cUC in promoting the wound healing of chronic complex foot ulcers. The clinical data included demographic information, past and present medical history including co-morbidities such as diabetes, hypertension, peripheral vascular disease, renal disease, and cardiovascular diseases, previous treatments and prior amputations. Special attention was given to assess the extent of the index ulcer by verifying the exposure of bone, tendon, muscle, or joint capsule, initial wound area ($cm^2$), wound location, presence of soft tissue infection and ischemia. In addition, data were also retrieved regarding assessment of wound measurement and photography to document the changes in the ulcer during the entire follow-up period.
Study Patients All study patients suffered from chronic, non-healing foot ulcers that demonstrated exposed bone, tendon, muscle, or joint capsule. These complex wounds were all associated with the clinical diagnosis of osteomyelitis confirmed by bone biopsy with positive microbial cultures and histopathological evidence of bone tissue containing lymphocytes or plasma cells.
Standard Evaluation and Management Following a full initial medical evaluation, all patients presented with ulcers complicated by osteomyelitis that were greater than 3 weeks in duration, larger than 2 cm wide and 3 mm deep, positive probe-to-bone or exposed bone. Patients were referred for an infectious disease consult while obtaining baseline X-ray and blood tests including complete blood count, C-reactive protein, erythrocyte sedimentation rate, and alkaline phosphatase. Those presenting with suspicion of peripheral vascular disease were also referred for a vascular consult. Patients cleared of notable vascular involvement with a high clinical suspicion of osteomyelitis (i.e., elevated white blood cell counts, C-reactive protein, erythrocyte sedimentation rate, or alkaline phosphatase) as well as radiographic evidence indicative of bone necrosis, were immediately scheduled for treatment as follows: in the operating room, all ulcers underwent sharp surgical debridement and the necrotic bone was resected when deemed medically necessary by the surgeon. For patients with forefoot ulcers, bone resection was performed until healthy bone was reached based on physical characteristics. For mid- and rear-foot ulcers, bone resection was performed in a "piecemeal" fashion with the intent of excising the majority of the diseased bone tissue while simultaneously preserving as much length as possible. Following resection, bone biopsy was performed to obtain a sample for microbial culture and histopathological confirmation of osteomyelitis. A small margin (~2 mm) of clinically presumed healthy bone was also obtained and submitted for pathological analysis to ensure the complete removal of diseased bone, as well as to guide the duration of systemic antibiotic administration. Afterward, any exposed bone received an open cortex procedure using either a 6-2 k-wire or surgical debridement device (Misonix. Inc., Farmingdale, N.Y.) to create ~3 (depending on the wound size) equidistant holes through the cortical bone to the underlying trabecular bone. This allowed for access to pluripotent adult progenitor stem cells to aid in repair as previously described. The exposed surgical wound was then completely covered by one layer of cUC (NEOX® CORD 1K, Amniox Medical, Inc., Atlanta, Ga.) that was held in place with either tissue adhesive (Indermil® tissue adhesive, United States Surgical Corporation, Conn.) or staples. All wounds were then covered with a standard non-adherent dressing (Xeroform dressing, DeRoyal Industries, Inc., Powell, Tenn.) followed by compression dressing (Coban™ 2 layer compression system, 3M, Co., St. Paul, Minn.) and a variety of off-loading devices. All patients initially received oral broad spectrum antibiotics until the bone culture results were available to guide subsequent administration of microbe-specific antibiotics. Patients with forefoot ulcers were discharged with an initial two-week antibiotic regimen pending the result of the bone margin histopathology. If the bone biopsy was free of any involvement, antibiotics were discontinued, but if the margin was not clear, the antibiotic therapy was continued for an additional 4-6 weeks. Patients with mid- or rear-foot osteomyelitis were discharged with continuous IV antibiotics for a 6-8 week duration.

All patients were discharged from the hospital once they were clinically stable, and returned to the wound clinic for weekly wound monitoring including dressing changes that followed the above standard of care with the addition of silver sulfadiazine (Silvadene®, Pfizer Inc., New York, N.Y.) to high colonization. If wound progression appeared to stall, an additional cUC application was applied during which time sharp debridement and open bone cortex were also performed. Patients received other treatments such as hyperbaric oxygen therapy and revascularization therapy if indicated by the study surgeon/PI.

Outcome Measures

Wound area was determined by using a ruler to measure the length and width of the wound. Complete wound healing was defined as 100% re-epithelialization as determined by the investigator. For those wounds achieving complete healing, the total time needed to achieve initial wound closure was assessed. In addition to wound closure, the relationship between the initial wound area and the time needed to achieve closure was assessed by subdividing the initial wound area into quartiles as previously described. The mean wound area and the mean time to achieve wound closure were compared between quartiles using an un-paired t-test; p-values<0.05 between groups were considered to be statistically significant.

Results

The patients had multiple co-morbidities including diabetes, hypertension, peripheral vascular disease, renal failure, and coronary artery disease. The ulcers were mostly ischemic, over half were gangrenous and some received prior partial amputation and revascularization attempts. The average ulcer size was 15.6±17.7 cm² (0.4-73.95 cm²). Overall, 26 wounds achieved complete closure (78.8%). Five patients were lost to follow up and one patient expired during the course of treatment, not believed to be treatment related, resulting in a healing rate in patients not lost to follow up of 96.3% with an average of 1.24 applications of cUC. Although 16 ulcers were recommended for amputation at presentation, two patients achieved complete wound closure using cUC without the need for amputation, one patient eventually received a below-knee amputation, and the remaining 13 wounds received partial digit resection.

Clinical Features

A total of 31 patients presenting with 33 foot ulcers were identified for inclusion in the study. A summary of their clinical data is provided in Table 1. There were 26 males and 5 females with an average age of 58.3±12.9 years. The majority of patients treated were Caucasian (12/31) or African-American (10/31). Overall, these patients presented with multiple co-morbidities, among which the most significant were diabetes (26/31), hypertension (23/31), peripheral vascular disease (16/31), renal failure (12/31), and coronary artery disease (9/31). In addition, 24/33 wounds (72.2%) were clinically judged as ischemic in the affected limb and 17/33 wounds (51.5%) had gangrene on the affected extremity.

TABLE 1

Summary of patient clinical data.

| | | |
|---|---|---|
| Gender | Male | 26 (83.9%) |
| | Female | 5 (16.1%) |
| Age | Median | 57 (range: 35-90) |
| | Mean | 58.3 ± 12.9 |
| Ethnicity | Caucasian | 12/31 (38.7%) |
| | African-American | 10/31 (32.3%) |
| | Hispanic | 6/31 (19.3%) |
| | Other | 3/31 (9.7%) |
| Significant Co-morbidities | Diabetes | 26/31 (83.9%) |
| | Hypertension | 23/31 (74.2%) |
| | Peripheral Vascular Disease | 16/31 (51.6%) |
| | Renal Failure | 12/31 (38.7%) |
| | Coronary Artery Disease | 9/31 (29%) |
| | Ischemia in affected limb (wounds) | 24/33 (72.7%) |
| | Gangrene (wounds) | 17/33 (51.5%) |
| Initial wound area | | 16.68 ± 18.07 cm² |
| Wound duration | | 4 weeks-1 year 7 months |
| Wound exposure | Muscle, tendon, ligament, bone | 27/33 (81.8%) |
| Osteomyelitis | | 33/33 (100%) |
| Wounds healed | | 26/27 (96.3%) |
| Average time to healing | | 16.02 ± 9.25 weeks (range: 4-44 weeks) |
| Average # applications of cUC | | 1.24 ± 0.44 |

All ulcers included in the study were chronic, non-healing wounds lasting for a duration of greater than 3 weeks and up to 1 year and 7 months. The average wound area for all wounds at the time of application of cUC was 15.6±17.7 cm² (0.4-73.95 cm²). At initial presentation, 9/33 ulcers (27.3%) were rearfoot, 21/33 ulcers (63.6%) were forefoot primarily associated with the digits, one ulcer was plantar, and 2 ulcers were non-healing Chopart amputation sites. All 33 ulcers were considered "complex" with exposed tendon, muscle, joint capsule or bone, and 27/33 ulcers (81.8%) demonstrated exposure of all four tissues. In addition, all patients had a diagnosis of osteomyelitis confirmed by bone biopsy showing the histopathological presence of inflammatory cells in the bone marrow and positive microbial cultures. Of 33 wounds, 16 (48.5%) presented with a recommendation for amputation by either the referring physician.

Wound Healing After Application of cUC

Figure 2:
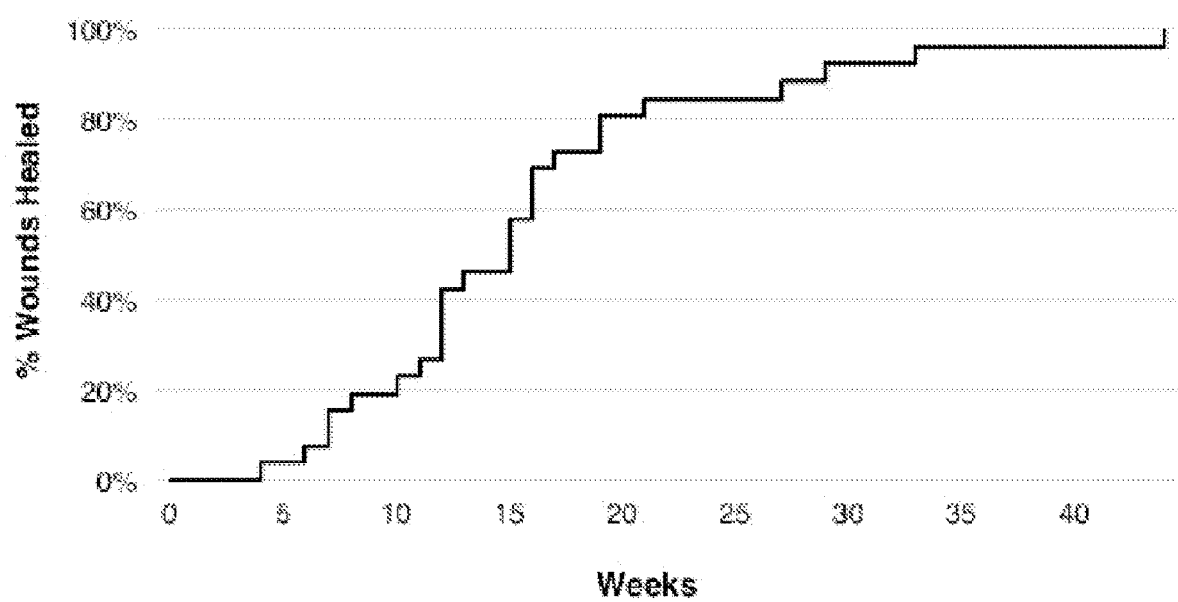
FIG. 2 illustrates time to wound closure for the 26 wounds that showed complete healing to determine the percentage of wounds healed over time, via a Kaplan-Meier analysis.

All 33 complex ulcers underwent sharp debridement, resection of necrotic bone with biopsy, open cortex and application of cUC without complications. A total of 26 wounds achieved complete wound closure as evidenced by complete epithelialization, resulting in an overall healing rate of 78.8%. Following initial application of cUC, five patients were lost to follow up post-cUC application and one patient expired due to causes not believed to be related to the study product. For the 27 wounds not lost to follow-up, the overall healing rate was 96.3%. For the 26 wounds that completely healed, the average time to wound closure was 16.0±9.3 weeks (range: 4-44 weeks) (FIG. 2). Twenty-one of the 26 wounds which healed received a single application of cUC, and 2 applications of cUC were needed to achieve healing of the remaining 5 wounds, with the second application occurring between 4-10 weeks after the initial application. The patient with the non-healing wound underwent a below-knee amputation due to wound complications and other co-morbidities.

To determine if initial wound area had any impact on the time to reach complete wound closure, the wounds were separated into four quartiles based on their initial area (0-25%, 25-50%, 50-75%, and 75-100%) of 2.2±0.9, 5.8±1.6, 13.8±3.9, and 43.0±23.1 cm², respectively (FIG.

Figure 3A:
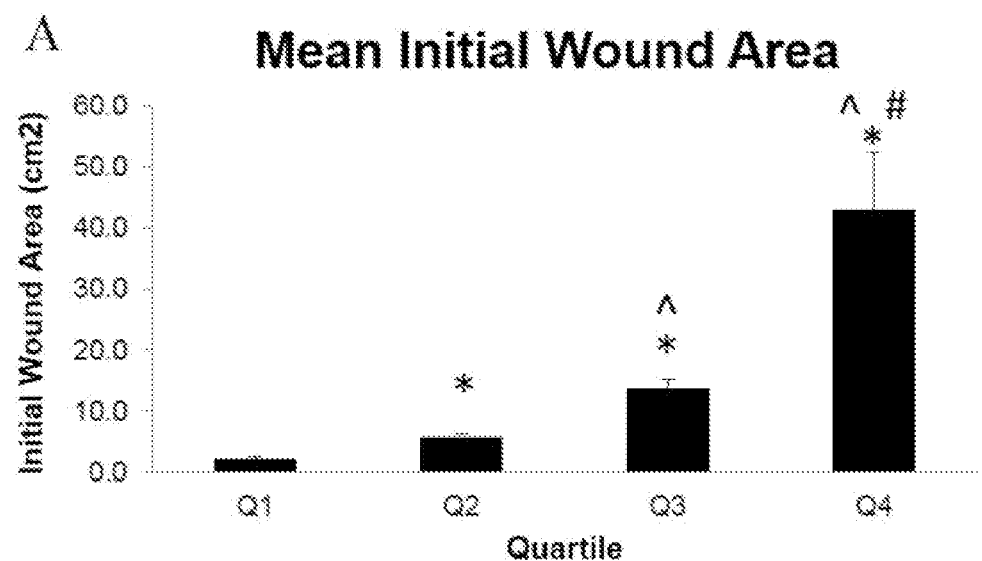
FIGS. 3A-3B illustrate wound closure based on initial wound area.
Figure 3B:
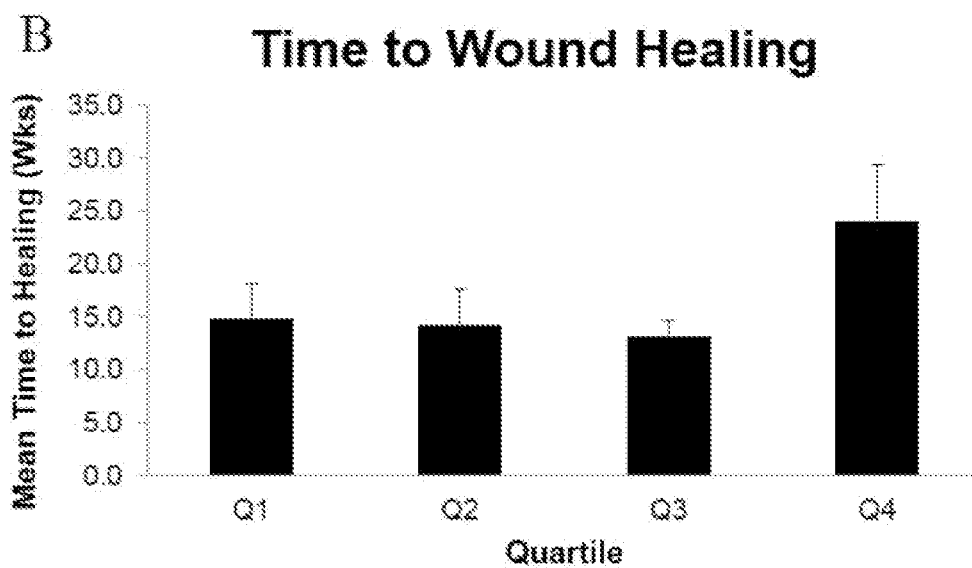

3A). As expected, there was a statistical difference among wound size in these four quartiles. However, the mean time to achieve wound closure was found to be similar without any statistically significant difference among them (FIG. 3B).

Although 16 ulcers were recommended for amputation at presentation, two patients achieved complete wound closure using cUC without the need for amputation. As stated above, one patient (6.25%) eventually received a below-knee amputation after a single cUC application. The remaining 13 wounds received partial digit resection, to a lesser extent than what was initially recommended.

Representative Cases

Case Study #1: $2^{nd}$ and $3^{rd}$ Metatarsal Wound with Gangrene

A 52 year-old female presented with several co-morbidities including type II diabetes, diabetic neuropathy, peripheral vascular disease, end stage renal disease, hypertension, hypercholesterolemia, and coronary artery disease. She was referred by the Infectious Diseases department of the hospital with a recommendation to amputate the $2^{nd}$ and $3^{rd}$ digits while presenting with a forefoot ulcer on the left $2^{nd}$ and $3^{rd}$ metatarsals with exposed muscle, tendon, ligament, and bone with gangrene. Following sharp debridement, bone resection, bone biopsy and open cortex procedure, cUC was applied to completely cover the index ulcer. Bone biopsy confirmed the diagnosis of osteomyelitis. At six weeks, the wound was reduced in size by approximately 50%. At seven weeks, the wound healing progression was noted to have stalled, and a second application of cUC was applied after debridement and open cortex surgical procedure. At 12 weeks, the index ulcer achieved complete epithelialization saving both the $2^{nd}$ and $3^{rd}$ digits without the need for any amputation. During the entire follow up period of 32 weeks, there was no recurrence.

Case Study #2. Wound Post-$4^{th}$ Ray Amputation

A 57 year-old male with diabetes, cellulitis, and ischemia presented with an open wound following left $4^{th}$ toe amputation with exposed bone, tendon, muscle, and ligament. After sharp debridement, bone resection, bone biopsy and open cortex procedure, cUC was applied to completely cover the wound. At 4 days and two weeks after application, the cUC could be observed filled with blood. However, the cUC remnant was left in place over the wound bed, and the wound continued to heal, achieving complete re-epithelialization by week 13.

Case Study #3 $1^{st}$ Ray Amputation

A 63 year-old male with a history of type I diabetes and peripheral vascular disease presented with an open wound in the midfoot following first ray amputation. In addition to osteomyelitis, gangrene was present on the affected limb. After sharp debridement, bone resection, bone biopsy, and open cortex procedure, the wound was covered by cUC. At 7 weeks, the wound displayed a 44% reduction in size. At 9 weeks, another application of cUC was performed following sharp debridement and open cortex surgical procedure. The index wound continued to show improvement at 11 weeks and went on to complete healing at 15 weeks. The wound remained healed with no recurrence at 28 weeks.

Example 2

Cryopreserved Human Umbilical Cord (HUC) vs. Biocellulose Film (BSCF) for Antenatal Spina Bifida Repair Two patches, HUC and BCF sutured over spina bifida (SB) lesions in a retinoic acid (RA) rat model, were compared for regenerative ingrowth of native cells and associated inflammatory response.

Pregnant time-dated Sprague-Dawley rats were gavaged with RA (40 mg/kg) on gestational day 10 (GD10) to induce SB in pups. Laparotomy and hysterotomy were performed on GD20 and HUC (n=11) or BCF (n=10) sutured over the spinal defect. Patches placed into the amniotic cavity without suturing over the lesion were controls. 30-34 hours after grafting pups were harvested and formalin fixed. H&E and Trichrome staining assessed cellular migration into the patches. Immunohistochemistry was performed to demonstrate the nature of the cellular migration. Native cell markers evaluated were CK 5/6 (epidermal), GFAP (astrocytes) and vWF (endothelial). Inflammatory markers were CD3 (lymphocytes), MPO (neutrophils), and F4-80 (macrophages). Four high power fields (hpf) of all patches and surrounding exudates were evaluated and Image-J software was used to quantify cells.

Pup survival was equal: HUC 8/11, BCF 7/10, (p=0.9). Histology showed cellular migration in all HUC patches applied over lesions (median:38 [range:13-102] cells/hpf) compared to none in BCF patches (Figure; p<0.001). CK 5/6 positive cells were noted migrating over the HUC patch surface (4-7 cells/hpf): GFAP positive cells were noted on the HUC patch surface adjacent to the lesion (3-11 cells/hpf); vWF positive cells were noted in the HUC patch (5-15 cells/hpf). No CK 5/6, GFAP or vWF positive cells were noted in BCF patches (p=0.03). HUC patches showed minimal MPO (2%[0-7%]), CD3 (7%[3-12%]) and F4-80 (0%) positive cells. Exudates in HUC treated pups had fewer MPO (0%[0-9%] vs 17%[0-39%]; p<0.01) and CD3 (7% [0-13%] vs 15%[0-22%]; p<0.01) positive cells compared to BCF and demonstrated no difference in F4-80. Both HUC and BCF control patches demonstrated no infiltrate.

Example 3

Cryopreserved Human Umbilical Cord for In-Utero Myeloschisis Repair

Described herein is a case of large lumbosacral myeloschisis with Chiari II malformation that underwent in-utero spina bifida repair at 23 weeks of gestation. The skin defect was closed using cryopreserved human umbilical cord patch following the primary closure of meningeal layers. The pregnancy was uncomplicated and the delivery occurred at 37 weeks by elective C-section. The repair site was intact with no evidence of cutaneous cerebrospinal fluid leakage. The skin regenerated into the patch after delivery over a period of 4 weeks. There was complete reversal of Chiari II malformation, normal lateral ventricles, normal sensory and motor response in the lower extremities, normal voiding cystourethrogram.

A 21 year old G1P0-0-0 was referred to the Fetal Center at Children's Memorial Hermann Hospital with myeloschisis of the fetus at 21 6/7 weeks gestation for possible in-utero spina bifida repair. On evaluation with both ultrasound and MRI, the skin defect extended from L3 level to S4 with no identifiable meningeal sac. The overall dimensions of the lesion measured 1.6 cm by 2.7 cm. The posterior superior iliac spine was prominent through the defect. She underwent an amniocentesis with the findings of a 46XX karyotype, elevated maternal serum alpha-fetoprotein at 8.25 multiples of median and a positive acetylcholinesterase. The fetal MRI showed a grade III Chiari II malformation with effacement of the cisterna magna and fourth ventricle and herniation of the cerebellar tonsils to the level of C2-C3. The left lateral ventricle measured 7.1 mm and the right measured 8.1 mm. Both lower extremities had good movement and there was no talipes. The patient met all the Management of Myelomeningocele Study (MOMS) for in-utero spina bifida repair. Due to the large size of the myeloschisis with the relationship of the skin margins to the posterior superior iliac spine, the need of using a patch to cover the skin was discussed. The patient was offered the HUC patch as an alternative to the usual Alloderm® after approval from the Fetal Therapy Board and the Institutional Review Board at University of Texas Medical School at Hosuton, Tex.

At 24 weeks of gestation, the surgery was conducted similar to the MOMs study protocol. Briefly, the patient underwent laparotomy under general anesthesia, followed by exposure of the uterus. The fetus was positioned so that the spina bifida lesion was close to the possible site of hysterotomy. Uterine entry was made between two full thickness stay sutures. The incision was extended using absorbable staples (Covidien, Dublin, Ireland). The fetal spina bifida defect site was exposed. A continuous intrauterine infusion of Lactated Ringers solution with Nafcillin 1 g/L was infused through a foley catheter. Fetal anesthesia consisting of fentanyl 20 μg/kg and paralytic agent (vecuronium 400 μg/kg) was administered intramuscularly. The defect was confirmed to be a myeloschisis with meningeal layers extending beyond the edges of the lesion with protruding posterior superior iliac spines. The skin lesion measured 5 cm×6 cm. An incision was made at the junction of meninges and skin. The meningeal layers were dissected off the fascia and closed primary approach in the midline using 6-O Monocryl suture (Ethicon, Somerville, N.J.). The skin edges were sutured to an HUC patch using 6-O Monocryl suture in a running locking (towards the patch) fashion, circumferentially. The fetus was repositioned in the uterus. Amnioinfusion was performed to refill the uterine cavity. The uterine incision was closed using 0-O Prolene sutures with multiple stay sutures and a running suture to reapproximate the edges. The laparotomy was closed in the usual fashion. Post-operatively, the patient had an uneventful course and was discharged home on post-operative day #5. The post-natal course was uncomplicated. On weekly ultrasound examination, the lesion site was noted to be covered with tissue with a thickness measuring 3-4 mm. There was a fluid-filled space noted posterior to the spinal cord and below the tissue at the repair site.

At 37½ weeks gestation, the patient was electively delivery by C-section. The lesion site appeared completely covered with no evidence of cutaneous CSF leakage. The patch appeared semi-transparent with visible clear fluid below it; the dural closure could be seen through the patch. The defect size measured 6 cm×5 cm. The anterior frontenelle was soft; the head circumference measured 33.5 cm. There was symmetric 5/5 power in all proximal muscle groups in the legs. There was slight right dorsiflexion weakness initially that improved at the time of discharge. Sensation to pin testing was noted in all lumbar dermatomes, S1 and perinatal region. The voiding cystourethrogram was normal and the post-void residual volume measuring <5 ml. The neonate was placed in supine position with lower spine elevated as a precautionary measure for 2 weeks. During the interim period, there was rapid regeneration of the skin into the graft. Wound care consisted of daily changed with a non-adherent dressing.

On day #1, the patch appeared opaque with increased vascularity in the periphery. On day #7, vascularization and epithelialization continued at the peripheral margins. There was a coat of fibrin deposited over the center of the patch. On day #14, there was complete epithelialization of the defect except for a 2 cm×1.5 cm in the lower part of the defect where there was vascular tissue covered with fibrin. Keratinization was noted to be proceeding from the periphery to the central portion of the defect over to the epithelialized tissue. On day #21, there was central area of granulation tissue measuring 1 cm×1 cm surrounded by epithelialization and keratinization. On day #28, the skin had completely healed over with keratinization except for 3×5 mm area that was still epithelializing.

Head ultrasound and MRI was performed on day #21. There was complete reversal of the Chiari II malformation, with atrophic changes in the left cerebellar hemisphere consistent with stigmata of hindbrain herniation prior to the surgery. The lateral ventricles measured within normal limits. There was a tissue bridge measuring 4-5 mm in thickness covering the defect site. There was no fluid filled space in the regenerated skin. There was a fluid space posterior to the spinal cord and the thecal layers. T1/T2 weighted images showed hypodense fibrous tissue, suggestive of tethering, between the spinal cord at the upper edge of the repair to the posterior thecal coverings of the spinal canal. The tethering adhesion measured 1 mm in thickness at the level of L3. The conus terminated at the level of L4. There was no tethering of the conus. Dysraphism of the posterior spinal elements was seen at L2-S1. The skin overlying the defect appeared intact without a definite subcutaneous tract.

The neonate was discharged home on day #22. The head circumference at discharge remained at 33 cm with a soft and scaphoid shaped anterior frontenelle. The lower extremities had normal movement. Neonatal urodynamic testing was within normal limits and the anal reflex was normal.

In this case, the primary objective of the patch was to create a water-tight and effective barrier between the spinal cord and the amniotic fluid which was successful. The HUC patch also showed reversal of Chiari II malformation and preservation of the lower extremities neurological function at birth. The lack of epithelialization and keratinization in utero was a surprising finding. Additionally, the rapid ingrowth of vascularization, epithelialization and keratinization after delivery was remarkable, which we were able to evidence on a daily basis. The presence of cerebrospinal fluid between the patch and dural closure and demonstration of fluctuance of anterior frontenelle supports the possibility of incomplete meningeal sealing. However, after the complete healing of the patch, there was no fluid space found between the repair site and meninges on the MRI. This supports the water-tight healing.

Example 4

Manufacturing Process of cUC cUC is aseptically processed in compliance with current Good Tissue Practices (cGTP) from donated human placental tissue after determination of donor eligibility and placenta/cord suitability.

Upon receipt of a tissue shipment, the shipping container is stored in a designated freezer.

Frozen tissue is thawed for processing. The UC is isolated from the placenta and opened. The arteries, vein, and a portion of the Wharton's Jelly that is associated with the blood vessels are removed, leaving the AM and remainder of the Wharton's Jelly. The blood is removed by soaking and swirling in solution and manual gentle removal.

The tissue is cut to achieve the designated product sizes.

Each unit of tissue is aseptically packaged in storage medium a sterile clear plastic peel pouch for a single application.

Example 5

Use of a Fetal Support Tissue Product to Reduce or Prevent Scar Formation in Granulation Tissue An individual having a wound exhibiting granulation tissue is identified. A fetal support tissue product is prepared. The fetal support tissue product applied to the granulation tissue. A protective covering is place over the fetal support tissue product.

Example 6

Use of a Fetal Support Tissue Product to Repair a Gingival Wound

An individual in need of repair of a gingival wound is identified. A fetal support tissue product is prepared. The wound is debrided as necessary. The fetal support tissue product is placed over the wound. A protective covering is place over the fetal support tissue product.

Example 7

Use of a Fetal Support Tissue Product to Repair a Damaged Joint Cavity

An individual in need of repair of a damaged joint cavity is identified. A fetal support tissue product is prepared. The joint cavity is prepared. The fetal support tissue product is placed over the joint cavity. A protective covering is place over the fetal support tissue product.

Example 8

Use of a Fetal Support Tissue Product to Treat a Complex Foot Ulcer

An individual having a complex foot ulcer is identified. A fetal support tissue product is prepared. The ulcer is debrided as necessary. Bone is resected as necessary. Optionally, an open cortex procedure is performed. The fetal support tissue product is placed over the ulcer. A protective covering is place over the fetal support tissue product.

Example 9

Cryopreserved Umbilical Cord (cUC) Treatment of Radiation Wound Post Melanoma Removal Involving Soft Tissue and Bone The patient was an 87-year old male with a history of renal transplantation due to polycystic kidney disease and most recently melanoma on his scalp. Surgical removal revealed the cancer had penetrated the bone. The melanoma's proximity to the brain did not allow for it all to be removed surgically, so the patient underwent radiation treatment. The radiation resulted in necrosis of the skull and a significant wound with exposed brain dura.

A 4×3 cm cUC graft (Neox1k; NX-10-4030) was cut into 6 strips and placed in an asterisk pattern over the wound and covered with a non-adhering dressing (Adaptic touch). Within 4 weeks the graft had absorbed and the wound bed had begun to granulate. 16 weeks after the initial application of the cUC graft, 100 mg of a particulate form of the tissue (CR-FL-100 mg; Clarix Flo) was injected into the bone to stimulate progress in the cranial margins. 21 weeks from the initial cUC application, progress was noted both in epithelialization and cranial margins. Therefore, another 100 mg of particulate cUC (Clarix Flo) was injected into the bone and a second 4×3 cm cUC tissue graft (NX-10-4030) was placed along the wound borders to progress this wound to complete healing.

This case study demonstrated the unique healing capabilities of cUC. Significantly, this patient's age, compromised renal function, and exposure to radiation created an extremely challenging wound environment. However, the introduction of cUC into the wound not only advanced the soft tissue of the wound to complete healing, but also showed the ability to stimulate bone regrowth, which was a novel observation.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a complex wound in an individual in need thereof, comprising: administering to a complex wound in the individual in need thereof, a therapeutically effective amount of a fetal support tissue product comprising previously frozen umbilical cord amniotic membrane, wherein the fetal support tissue product is formulated as an allograft from which water has not been substantially removed, wherein the complex wound comprises a wound that is characterized by exposed bone, muscle, tendon, joint capsule, or a combination thereof, wherein the complex wound is re-vascularized and re-epithelialized by the fetal support tissue product.

2. The method of claim 1, wherein the complex wound is an ulcer, a lower extremity ulcer, a foot ulcer, a chronic foot ulcer, a pressure sore, a diabetic foot ulcer, or an ischemic wound, a neurotropic ulcer, an arterial ulcer, or combination thereof.

3. The method of claim 1, wherein the complex wound comprises exposed bone.

4. The method of claim 3, wherein the complex wound comprises bone loss.

5. The method of claim 1, further comprising debriding the complex wound, wherein the debriding is surgical debridement.

6. The method of claim 1, further comprising resecting bone wherein the resecting is performed until healthy bone is reached, and further, wherein the resecting is performed to substantially remove necrotic or diseased bone.

7. The method of claim 1, further comprising opening the cortex of exposed bone.

8. The method of claim 1, further comprising covering the fetal support tissue product with a dressing, antimicrobial dressing, antimicrobial alginate dressing, compression dressing, gauze, patch, substrate, backing, covering, bandage, or a combination thereof.

9. The method of claim 1, further comprising administering a treatment selected from the group consisting of antibiotics, hyperbaric oxygen therapy, revascularization therapy, and combinations thereof.

10. The method of claim 1, wherein the individual has osteomyelitis.

11. The method of claim 1, wherein the fetal support tissue product is aseptically processed or terminally sterilized.

12. The method of claim 1, wherein the fetal support tissue product is from human, non-human primate, cow, or pig.

13. The method of claim 1, wherein the fetal support tissue product further comprises Wharton's Jelly.

14. The method of claim 1, wherein the fetal support tissue product is substantially free of blood, lacks an umbilical cord vein, or lacks umbilical cord arteries.

15. The method of claim 1, wherein the complex wound is a chronic wound.

16. The method of claim 1, wherein the complex wound is the result of an injury, surgery, a burn, radiation or a combination thereof.

17. The method of claim 1, wherein the complex wound is associated with an infection.

18. The method of claim 1, wherein the fetal support tissue product comprises biologically active HC-HA/PTX3.

19. The method of claim 1, wherein the fetal support tissue product is formulated as a sheet.

20. The method of claim 19, wherein the fetal support tissue product sheet is administered to the complex wound such that it covers less than the whole area of the complex wound.

21. The method of claim 19, wherein the fetal support tissue product sheet is placed along the wound borders to progress the wound to complete healing.

22. The method of claim 19, wherein the fetal support tissue product sheet is absorbed by the complex wound.

23. The method of claim 22, wherein the fetal support tissue product sheet is absorbed by the complex wound within 4 weeks after the first application of the fetal support tissue product.

24. The method of claim 1, wherein the complex wound is re-keratinized.

25. The method of claim 1, wherein the complex wound is re-epithelialized after 1 or 2 applications of the fetal support tissue product.

26. The method of claim 1, wherein the complex wound is revascularized after 1 or 2 applications of the fetal support tissue product.

* * * * *